(12) United States Patent
Asakura et al.

(10) Patent No.: US 11,174,310 B2
(45) Date of Patent: Nov. 16, 2021

(54) DISULFIDE-TYPE HMGB1-SPECIFIC ANTIBODY, METHOD FOR MEASURING DISULFIDE-TYPE HMGB1 AND KIT FOR SAID MEASUREMENT, AND MEASUREMENT METHOD CAPABLE OF QUANTITATING ALL OF HMGB1 MOLECULES INCLUDING REDUCED HMGB1, DISULFIDE-TYPE HMGB1 AND THROMBIN-CLEAVABLE HMGB1 AND KIT FOR SAID MEASUREMENT

(71) Applicant: Fuso Pharmaceutical Industries, Ltd., Osaka (JP)

(72) Inventors: Masahiro Asakura, Osaka (JP); Aya Keshi, Osaka (JP); Kanako Abe, Osaka (JP); Nana Sakamoto, Osaka (JP); Shiho Yamazaki, Osaka (JP); Hirotsugu Uehara, Osaka (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 191 days.

(21) Appl. No.: 16/345,570

(22) PCT Filed: Oct. 19, 2017

(86) PCT No.: PCT/JP2017/037789
§ 371 (c)(1),
(2) Date: Apr. 26, 2019

(87) PCT Pub. No.: WO2018/079393
PCT Pub. Date: May 3, 2018

(65) Prior Publication Data
US 2019/0375834 A1    Dec. 12, 2019

(30) Foreign Application Priority Data
Oct. 26, 2016 (JP) .............................. JP2016-209510

(51) Int. Cl.
C07K 16/24    (2006.01)
G01N 33/68    (2006.01)

(52) U.S. Cl.
CPC ......... *C07K 16/24* (2013.01); *G01N 33/6863* (2013.01); *C07K 2317/21* (2013.01); *C07K 2317/24* (2013.01); *C07K 2317/76* (2013.01); *G01N 2333/52* (2013.01)

(58) Field of Classification Search
None
See application file for complete search history.

(56) References Cited

U.S. PATENT DOCUMENTS 4,722,889 A    2/1988  Lee et al.
7,964,706 B2   6/2011  Wu et al.
2005/0037448 A1  2/2005  Bouanani et al.
2007/0172888 A1  7/2007  Hallermayer et al.
2012/0238037 A1  9/2012  Kobayashi
2013/0130275 A1  5/2013  Yoshimura et al.
2014/0348704 A1  11/2014 Kobayashi et al.
2018/0246121 A1  8/2018  Asakura et al.
2020/0363416 A1* 11/2020 Yang ................ G01N 33/57438

FOREIGN PATENT DOCUMENTS

| EP | 3067697 A1 | 9/2016 |
| JP | H0552844 | 3/1993 |
| JP | 2002511143 | 4/2002 |
| JP | 2003096099 | 4/2003 |
| JP | 2009050269 | 3/2009 |
| JP | 2009524807 | 7/2009 |
| JP | 2011095014 | 5/2011 |
| JP | 2011-241219 A | 12/2011 |
| JP | 2011241219 A | 12/2011 |
| JP | 5055598 B2 | 10/2012 |
| JP | 2013122402 | 6/2013 |
| WO | WO-2005/026209 A2 | 3/2005 |
| WO | WO-2007085411 A1 | 8/2007 |
| WO | WO-2011052486 A1 | 5/2011 |
| WO | WO-2013084969 A1 | 6/2013 |
| WO | WO-2014/147873 A1 | 9/2014 |
| WO | WO-2014147873 A1 | 9/2014 |
| WO | WO-2015068715 | 5/2015 |
| WO | WO-2016/118531 A1 | 7/2016 |
| WO | WO-2016118531 A1 | 7/2016 |
| WO | WO-2017/033846 A1 | 3/2017 |

(Continued)

OTHER PUBLICATIONS

International Patent Application No. PCT/JP2017/037789, International Search Report and Written Opinion dated Jan. 23, 2018, 5 pgs.
Asakura, et al., "HMGB1 Assay Kit—"FUSO"", Wako Pure Chemical Industries, Ltd., e-published on Oct. 21, 2016 [retrieved on Jan. 11, 2018]. Retrieved from the Internet:, <http://www.wako-chem.co.jp/siyaku/journal/index.htm>, <http://www.wako-chem.co.jp/siyaku/journal/biowin/pdf/bio147>, <http://www.wako-chem.co.jp/siyaku/biowindx_2.htm>, with English translation, 4 pgs.
Venereau, E., et al., "Mutually exclusive redox forms of HMGB1 promote cell recruitment or proinflammatory cytokine release", J. Exp. Med., 209, (2012), 1519-1528.
Wang, H., et al., "HMG-1 as a Late Mediator of Endotoxin Lethality in Mice", Science, 285, (Jul. 9, 1999), 248-251.

(Continued)

*Primary Examiner* — Andrea S Grossman
(74) *Attorney, Agent, or Firm* — Schwegman Lundberg & Woessner, P.A.

(57) ABSTRACT

The present invention provides antibodies that show specific reactivity to disulfide-type HMGB1. Furthermore, the present invention provides methods for specifically measuring disulfide-type HMGB1 using the antibodies, and kits or reagents for the measurement. The present invention also provides methods for measuring total HMGB1 using such an antibody and an antibody that binds to both disulfide-type HMGB1 and reduced-type HMGB1 but does not bind to des-HMGB1, and kits or reagents for the measurement.

11 Claims, 16 Drawing Sheets

Specification includes a Sequence Listing.

(56) References Cited

FOREIGN PATENT DOCUMENTS

| WO | WO-2017033846 | 3/2017 |
| WO | WO-2017/077001 A1 | 5/2017 |
| WO | WO-2017077001 A1 | 5/2017 |

OTHER PUBLICATIONS

Wang, Z., et al., "Universal PCR amplification of mouse immunoglobulin gene variable regions: the design of degenerate primers and an assessment of the effect of DNA polymerase 3' to 5' exonuclease activity", Journal of Immunological Methods, 233, (2000), 167-177.

Yang, H., et al., "MD-2 is required for disulfide HMGB1-dependent TLR4 signaling", J. Exp. Med., 212, (2015), 5-14.

Yang, H., et al., "The many faces of HMGB1: molecular structure-functional activity in inflammation, apoptosis, and chemotaxis", J. Leukoc. Biol., 93, (2013), 865-873.

U.S. Appl. No. 15/753,368, Response filed Feb. 9, 2021 to Final Office Action dated Aug. 10, 2020, 9 pgs.

"U.S. Appl. No. 15/753,368, Restriction Requirement dated Sep. 11, 2019", 9 pgs.

"U.S. Appl. No. 15/753,368, Response filed Nov. 7, 2019 to Restriction Requirement dated Sep. 11, 2019", 5 pgs.

"U.S. Appl. No. 15/753,368, Non Final Office Action dated Jan. 21, 2020", 7 pgs.

"U.S. Appl. No. 15/753,368, Response filed Jul. 2, 2020 to Non Final Office Action dated Jan. 21, 2020", 9 pgs.

"U.S. Appl. No. 15/753,368, Final Office Action dated Aug. 10, 2020", 8 pgs.

"International Application No. PCT/JP2016/074181, International Search Report and Written Opinion dated Oct. 18, 2016", (Oct. 18, 2016), 9 pgs.

"International Application Serial No. PCT/JP2017/037789, International Preliminary Report on Patentability dated May 9, 2019", 15 pgs.

"International Patent Application No. PCT/JP2016/074181, International Preliminary Report on Patentability dated Mar. 8, 2018", 6 pgs.

"Peptide Competition Assay (PCA)", Rockland Antibodies & Assays, Rockland Immunochemicals Inc., [Online] Retrieved from the internet on Jun. 1, 2015: <URL: http://www.rockland-inc.com/uploadedFiles/Support/Protocols/Peptide-Competition-Protocol.pdf>, (Jun. 1, 2015), 2 pgs.

Gibot, Sébastien, et al., "High-mobility group box 1 protein plasma concentrations during septic shock", Intensive Care Med, 33(8), (Aug. 2007), 1347-1353.

Nakamura, T., et al., "Hemoperfusion Treatment in a Septic Shock Patient with Autosomal Dominant Polycystic Kidney Disease and Increased HMGB1 Protein Levels", Blood Purification; 32(2), Retrieved on May 11, 2018, (Aug. 2011), 139-142.

Wang, Haichao, et al., "HMG-1 as a Late Mediator of Endotoxin Lethality in Mice", Science, 285(5425), (1999), 248-251.

Yamada, Shingo, et al., "High Mobility Group Protein 1 (HMGB1) Quantified by ELISA with a Monoclonal Antibody That Does Not Cross-React with HMGB2", Clinical Chemistry 49, No. 9, 2003, (2003), 1535-1537.

U.S. Appl. No. 15/753,368, Non Final Office Action dated Jun. 9, 2021, 15 pgs.

\* cited by examiner

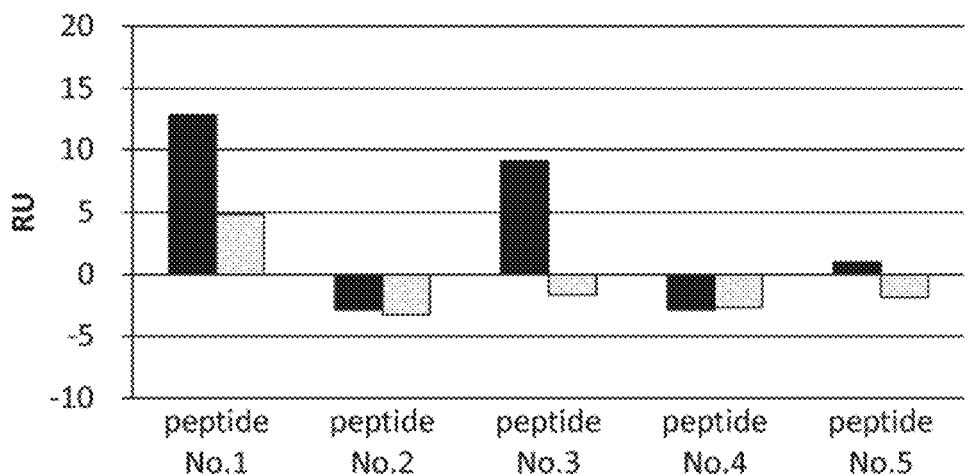
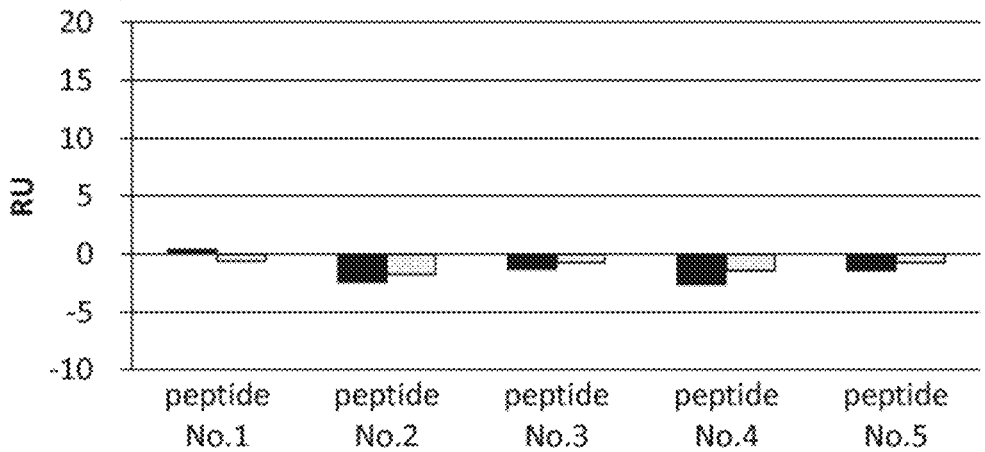
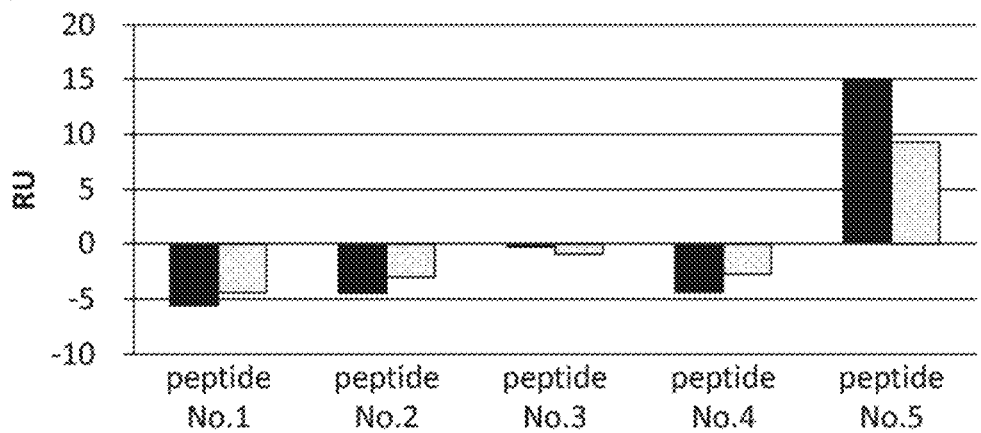
FIG. 2

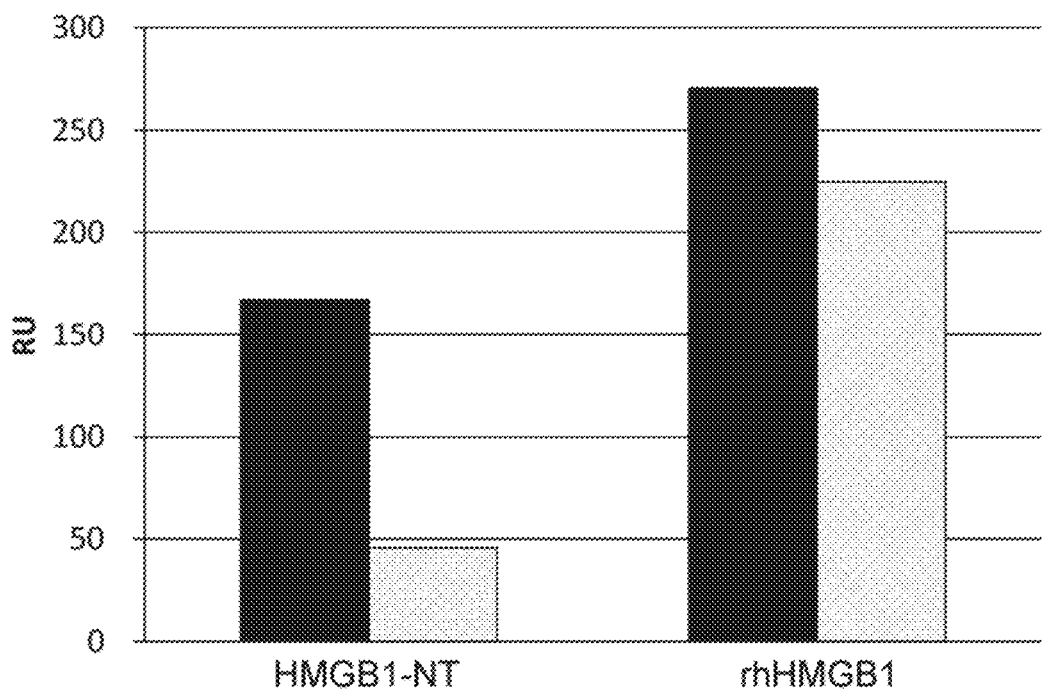
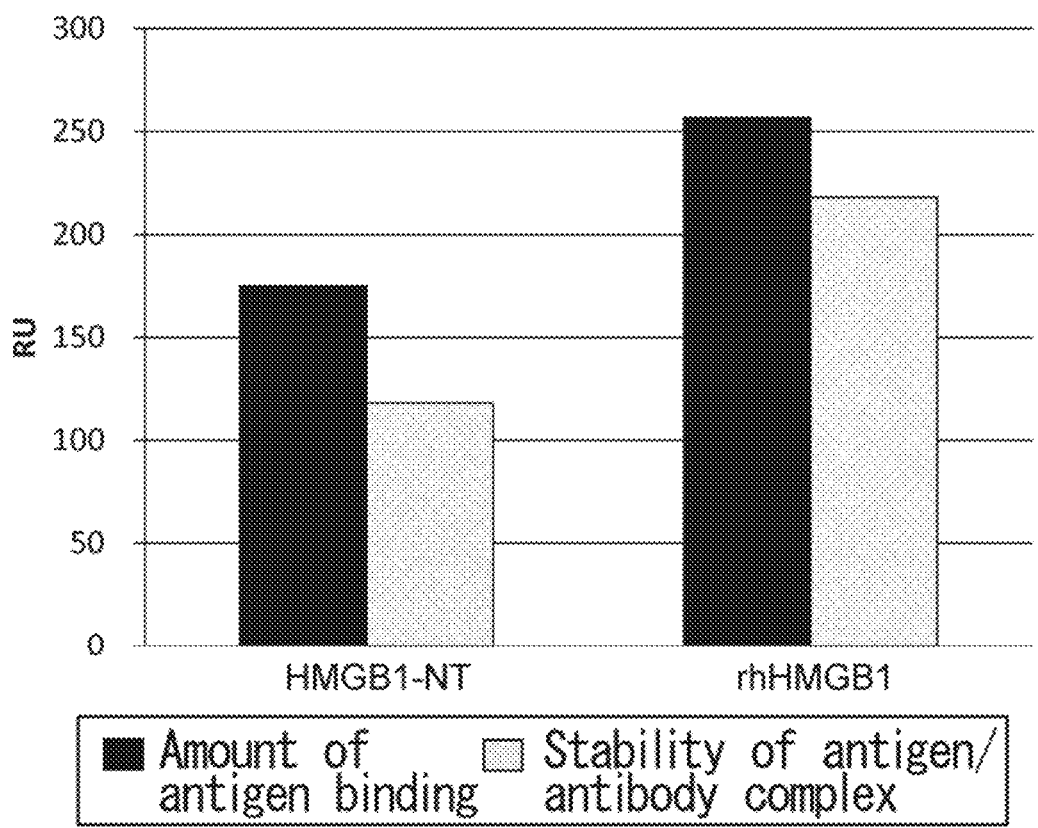
FIG. 3

Alignment of the HMa186 V$_H$ region analyzed by IGBLAST

```
                               <----------------------------FR1-IMGT-------------------------><-----CDR1-IMGT---
                                 L  E  S  G  P  G  I  L  Q  P  S  Q  T  L  S  L  T  C  S  F  S  G  F  S  L  S  T  S  G
HMa186 VH     10   CTGGAGAGTCAGGGCCCCTGGGATATTGCAGCCCTCAGTGACCCTGTCTCTTCACTGAGCACTTCTGGT

---->                 <-------------------FR2-IMGT-----------------------><-----CDR2-IMGT------><---
                     M  G  V  G  W  I  R  Q  P  S  G  K  G  L  E  W  L  A  H  I  W  W  D  D  D  K  Y  Y  N  T
HMa186 VH    100   ATGGGTGTAGGCTGGATCCGTCAGCCCTCAGGAAAGGGTCTGGAGTGGCTGGCACACATTTGGTGGGATGATGATAAGTACTATAACACA

-------------------------FR3-IMGT-----------------------------------------><-----
                     A  L  K  S  G  L  T  I  S  K  D  T  S  K  N  Q  V  F  L  K  I  A  S  V  D  T  A  D  T  A
HMa186 VH    190   GCCCTGAAGAGTGGCCTCACAATCTCCAAAGATACCTCCAAGAATCAGGTCTTCCTGAAGATCGCCAGTGTGGACACTGCAGATACTGCC

CDR3-IMGT--------->
                     T  Y  Y  C  A  R  I  A  V  G  Y  F  Y  V  W  G  A  G  T  T  V  T  V  S  S  (SEQ ID NO:70)
HMa186 VH    280   ACATACTACTGTGCTCGAATAGCGGTAGGGTACTTCTATGTCTGGGGCGCAGGGACCACGGTCACCGTCTCCTCAG  (SEQ ID NO:71)
```

FIG. 14

Alignment of the HMa186 V_k region analyzed by IGBLAST

```
              <---------------FR1-IMGT-------------------
               Q  I  V  L  T  Q  S  P  A  S  L  A  V  S  L  G  Q  R  A  T  I  S  Y  R  A  S  K  S  V  S
HMa186VK 183 GACATTGTGCTGACACAGTCTCCTGCTTCCTTAGCTGTATCTCTGGGGCAGAGGGCCACCATCTCATACAGGGCCAGCAAAAGTGTCAGT  272

------><---------CDR1-IMGT------><----------
                 T  S  G  Y  S  Y  M  H  W  N  Q  Q  K  P  G  Q  P  P  R  L  L  I  Y  L  V  S  N  L  E  S
HMa186VK 273 ACATCTGGCTATAGTTATATGCACTGGAACCAACAGAAACCAGGACAGCCACCCAGACTCCTCATCTATCTTGTATCCAACCTAGAATCT  362

----------------------FR3-IMGT--------------------------
              G  V  P  A  R  F  S  G  S  G  S  G  T  D  F  T  L  N  I  H  P  V  E  E  D  A  A  P     (SEQ ID NO: 72)
HMa186VK 363 GGGGTCCCTGCCAGGTTCAGTGGCAGTGGGTCTGGGACAGACTTCACCCTCAACATCCATCCTGTGGAGGAGGATGCTGCACCA         (SEQ ID NO: 73) 449
```

DISULFIDE-TYPE HMGB1-SPECIFIC ANTIBODY, METHOD FOR MEASURING DISULFIDE-TYPE HMGB1 AND KIT FOR SAID MEASUREMENT, AND MEASUREMENT METHOD CAPABLE OF QUANTITATING ALL OF HMGB1 MOLECULES INCLUDING REDUCED HMGB1, DISULFIDE-TYPE HMGB1 AND THROMBIN-CLEAVABLE HMGB1 AND KIT FOR SAID MEASUREMENT

This application is a U.S. National Stage Filing under 35 U.S.C. 371 from International Application No. PCT/W2017/037789, filed on Oct. 19, 2017, and published as WO 2018/079393 A1 on May 3, 2018, which claims the benefit of priority to Japanese Application No. 2016-209510, filed on Oct. 26, 2016, each of which is incorporated by reference herein in its entirety.

TECHNICAL FIELD

The present invention relates to antibodies specific to disulfide-type HMGB1 which evokes inflammatory response and allows cytokines such as TNF to be released, methods and reagents for measuring disulfide-type HMGB1, and measurement methods and measurement reagents capable of quantitating total HMGB1 including reduced-type HMGB1, disulfide-type HMGB1, thrombin-cleaved HMGB1, etc. The present invention belongs to the field of life science such as clinical examination, clinical pathology, immunology, and medicine, in particular, the field of treatment, diagnosis, research, and such of serious pathological conditions such as inflammation and sepsis.

BACKGROUND ART

High Mobility Group Protein BOX 1 (hereinafter, "HMGB1") is a non-histone protein contained in the chromatin structure, and is commonly included in many higher plants and animals. HMGB1 acts on dendritic cells and monocytes, and induces maturation, infiltration, and release of cytokines and inflammatory mediators.

In 1999, Wang et al. (Non-patent Document 1) showed that HMGB1 can be a marker for sepsis, and HMGB1 has come to draw attention as a mediator expressed in the late stage of septic shock. Furthermore, since HMGB1 is released from the nuclei in the event of sepsis and exhibits severe cytotoxicity, it has been suggested to be involved in lethality during sepsis.

Sepsis is an acute inflammatory response accompanying general symptoms in which exogenous factors such as bacterial infection, pathogen-associated molecular patterns (PAMPs), necrotic cells generated in vivo, molecules derived from damaged tissues (Damage Associated Molecular Patterns: DAMPs), and such cause release of cytokines which are endogenous inflammation mediators into the blood flow. HMGB1 is thought to be a type of DAMPs.

Meanwhile, it is known that HMGB1 exists in a plurality of redox states, and only the disulfide-type of HMGB1 induces inflammation (Non-patent Document 2). Yang et al. discovered that only the disulfide-type of HMGB1 binds to MD-2 in vitro with high affinity, and promotes secretion of the inflammatory cytokine tumor necrosis factor (TNF) by mouse macrophages (Non-Patent Document 3). Furthermore, reduced-type HMGB1 is known to have the ability to induce chemokines (Non-patent Document 4).

Furthermore, WO2014/147873 A1 (Patent Document 1) reports that, cleaving HMGB1 between arginine at position 10 ($R_{10}$) and glycine at position 11 ($G_{11}$) by thrombin (i.e., cutting out the N-terminal amino acids of M1 to R10 of HMGB1 from the full-length HMGB1) produces a cleaved product of HMGB1 which has newly exposed N-terminal amino acid residues "GKMSS . . . " (SEQ ID NO: 76), and the cleaved product was named "des-HMGB1". Moreover, WO2014/147873 A1 reports that des-HMGB1 is inactivated and has lowered cytotoxicity.

Measurement of disulfide-type HMGB1 is particularly important for grasping the conditions of patients with serious diseases such as sepsis, and for performing therapeutic intervention such as blood purification therapy as necessary. Further, for example, patient's pathological background can be grasped accurately by examining the ratio between the amount of disulfide-type HMGB1 and the amount of total HMGB1 including cleaved des-HMGB1 and reduced-type HMGB1 in addition to disulfide-type HMGB1. However, kits that can specifically measure disulfide-type HMGB1 alone, and kits that can measure various structurally different HMGB1 have not been made.

CITATION LIST

Patent Document

[Patent Document 1] WO2014/147873 A1

Non-Patent Documents

[Non-patent Document 1] SCIENCE, 285, 248-251, 1999
[Non-patent Document 2] Journal of Leukocyte Biology, Volume 93, page 865-873, June 2013
[Non-patent Document 3] The Journal of Experimental Medicine, Vol. 212, No. 1, 5-14, 2015
[Non-patent Document 4] The Journal of Experimental Medicine, Vol. 209 No. 9 1519-1528, 2012

SUMMARY OF THE INVENTION

Problems to be Solved by the Invention

As mentioned above, antibodies that specifically recognize disulfide-type HMGB1 alone, kits that can specifically measure disulfide-type HMGB1 alone, and kits that can measure various structurally different HMGB1 have not been made. Therefore, to date, it has been possible that disulfide-type HMGB1 which has the ability to induce cytokines could be measured together with other HMGB1 having structures with poor biological activity. Accordingly, one cannot deny the possibility that the relationship between pathological conditions and blood HMGB1 concentration has not been understood accurately.

Furthermore, when preparing monoclonal antibodies and such, peptides and the like are sometimes used for the immunization; however, the use of a portion containing a plurality of cysteins as an immunogen is usually avoided since the antigen could be oxidized and adopt unexpected structures. In addition, for antibody production, the antigen needs to undergo intracellular processing and be presented by antigen-presenting cells. The antigen could be oxidized or reduced and adopt an unexpected structure also in this case. Therefore, producing antibodies that recognize disulfide bond-containing structures, including disulfide-type HMGB1, is generally difficult.

Thus, while there has been a desire for establishing a means for specifically measuring disulfide-type HMGB1, it has been difficult to produce antibodies against HMGB1 which has a disulfide bond. Furthermore, to accurately grasp the pathological background of a patient, various structurally different HMGB1 needs to be measured.

The present invention was made in view of such circumstances. An objective of the present invention is to provide disulfide-type HMGB1-specific antibodies, methods and reagents for measuring disulfide-type HMGB1, and measurement methods and measurement reagents capable of quantitating total HMGB1 including reduced-type HMGB1, disulfide-type HMGB1, and thrombin-cleaved HMGB1 (des-HMGB1).

Means for Solving the Problems

The present inventors conducted dedicated research to solve the above-mentioned problems. As a result, the present inventors discovered antibodies that show specific reactivity to disulfide-type HMGB1, and established methods for specifically measuring disulfide-type HMGB1 using the antibodies. Furthermore, the present inventors produced measurement methods capable of quantitating total HMGB1 by combining a plurality of distinct antibodies such as a disulfide-type HMGB1-specific antibody and an antibody that bind to both disulfide-type HMGB1 and reduced-type HMGB1 but do not bind to des-HMGB1. The present invention is based on such findings, and relates to the following:

[1] an antibody which specifically binds to disulfide-type HMGB1;
[2] the antibody of [1], which recognizes an antigenic determinant comprising a disulfide bond formed by cysteines at position 23 ($C_{23}$) and position 45 ($C_{45}$) of disulfide-type HMGB1;
[3] the antibody of [1] or [2], which has neutralizing activity against disulfide-type HMGB1 having activity to bind to MD-2, and/or disulfide-type HMGB1 having cytokine-inducing ability;
[4-1] the antibody of any one of [1] to [3], which comprises heavy chain CDR1, CDR2, and CDR3 having the same amino acid sequences as heavy chain CDR1, CDR2, and CDR3 of monoclonal antibody HMa186 produced by a hybridoma identified by accession number NITE BP-02019, and light chain CDR1, CDR2, and CDR3 having the same amino acid sequences as light chain CDR1, CDR2, and CDR3 of monoclonal antibody HMa186 produced by a hybridoma identified by accession number NITE BP-02019;
[4-2] the antibody of any one of [1] to [4-1], which comprises heavy chain CDR1 having the amino acid sequence of SEQ ID NO: 25, heavy chain CDR2 having the amino acid sequence of SEQ ID NO: 27, heavy chain CDR3 having the amino acid sequence of SEQ ID NO: 29, light chain CDR1 having the amino acid sequence of SEQ ID NO: 31, and light chain CDR2 having the amino acid sequence of SEQ ID NO: 33;
[4-3] the antibody of any one of [1] to [4-2], which comprises heavy chain FR1 having the amino acid sequence of SEQ ID NO: 35, heavy chain FR2 having the amino acid sequence of SEQ ID NO: 37, heavy chain FR3 having the amino acid sequence of SEQ ID NO: 39, light chain FR1 having the amino acid sequence of SEQ ID NO: 41, light chain FR2 having the amino acid sequence of SEQ ID NO: 43, and light chain FR3 having the amino acid sequence of SEQ ID NO: 45;
[5-1] the antibody of any one of [1] to [4-3], which comprises a heavy chain variable region having the same amino acid sequence as the heavy chain variable region of monoclonal antibody HMa186 produced by a hybridoma identified by accession number NITE BP-02019, and a light chain variable region having the same amino acid sequence as the light chain variable region of monoclonal antibody HMa186 produced by a hybridoma identified by accession number NITE BP-02019;
[5-2] the antibody of any one of [1] to [5-1], which comprises a heavy chain variable region comprising the amino acid sequence of SEQ ID NO: 47 or 70, and a light chain variable region comprising the amino acid sequence of SEQ ID NO: 49 or 72;
[6] a monoclonal antibody HMa186 produced by a hybridoma identified by accession number NITE BP-02019;
[7] a low-molecular-weight antibody of the antibody of any one of [1] to [6];
[8] a fragment of the antibody of any one of [1] to [7], which has specific binding activity to disulfide-type HMGB1;
[9] a chimeric antibody or humanized antibody of the antibody of any one of [1] to [6];
[10] a human antibody of the antibody of any one of [1] to [6];
[11] a method for producing the antibody of [9], which comprises the steps of linking a DNA encoding a variable region of the antibody of any one of [1] to [6] with a DNA encoding a constant region; inserting this into an expression vector; introducing the vector into a host; and producing the variable region and the constant region of the antibody;
[12] a method for measuring or detecting disulfide-type HMGB1 in a sample, which comprises the step of contacting the sample with the antibody of any one of [1] to [7], [9], and [10];
[13] the method of [12], wherein measuring or detecting disulfide-type HMGB1 is conducted by an immunological test method;
[14] a kit or reagent for measuring or detecting disulfide-type HMGB1, which comprises the antibody of any one of [1] to [7], [9], and [10];
[15] the kit or reagent of [14], for use in an immunological test method;
[16] a method for measuring or detecting total HMGB1 in a sample, which comprises contacting the sample with the antibodies of (a) and (b) below:
    (a) the antibody of any one of [1] to [7], [9], and [10]; and
    (b) an antibody that binds to both disulfide-type HMGB1 and reduced-type HMGB1 but does not bind to des-HMGB1;
[17] the method of [16], wherein total HMGB1 includes disulfide-type HMGB1, reduced-type HMGB1, and thrombin-cleaved HMGB1;
[18] the method of [16] or [17], wherein the antibody that binds to both disulfide-type HMGB1 and reduced-type HMGB1 but does not bind to des-HMGB1 is an antibody which recognizes an antigenic determinant comprising the amino acid residues between glycine at position 2 ($G_2$) and alanine at position 17 ($A_{17}$) of disulfide-type HMGB1;
[19-1] the method of any one of [16] to [18], wherein the antibody that binds to both disulfide-type HMGB1 and reduced-type HMGB1 but does not bind to des-HMGB1 is an antibody which comprises heavy chain CDR1, CDR2, and CDR3 having the same amino acid sequences as heavy chain CDR1, CDR2, and CDR3 of monoclonal antibody HMa166 produced by a hybridoma identified by accession number NITE BP-02020, and light chain CDR1, CDR2, and CDR3 having the same amino acid sequences as light chain CDR1, CDR2, and CDR3 of monoclonal antibody HMa166 produced by a hybridoma identified by accession number NITE BP-02020;

[19-2] the method of any one of [16] to [19-1], wherein the antibody that binds to both disulfide-type HMGB1 and reduced-type HMGB1 but does not bind to des-HMGB1 is an antibody which comprises heavy chain CDR1 having the amino acid sequence of SEQ ID NO: 51, heavy chain CDR2 having the amino acid sequence of SEQ ID NO: 53, and heavy chain CDR3 having the amino acid sequence of SEQ ID NO: 55;

[19-3] the method of any one of [16] to [19-2], wherein the antibody that binds to both disulfide-type HMGB1 and reduced-type HMGB1 but does not bind to des-HMGB1 is an antibody which comprises heavy chain FR1 having the amino acid sequence of SEQ ID NO: 57, heavy chain FR2 having the amino acid sequence of SEQ ID NO: 59, and heavy chain FR3 having the amino acid sequence of SEQ ID NO: 61;

[20-1] the method of any one of [16] to [19-3], wherein the antibody that binds to both disulfide-type HMGB1 and reduced-type HMGB1 but does not bind to des-HMGB1 is an antibody which comprises a heavy chain variable region having the same amino acid sequence as the heavy chain variable region of monoclonal antibody HMa166 produced by a hybridoma identified by accession number NITE BP-02020, and a light chain variable region having the same amino acid sequence as the light chain variable region of monoclonal antibody HMa166 produced by a hybridoma identified by accession number NITE BP-02020;

[20-2] the method of any one of [16] to [20-1], wherein the antibody that binds to both disulfide-type HMGB1 and reduced-type HMGB1 but does not bind to des-HMGB1 is an antibody which comprises a heavy chain variable region comprising the amino acid sequence of SEQ ID NO: 63 or 74;

[21] the method of any one of [16] to [20-2], wherein the antibody that binds to both disulfide-type HMGB1 and reduced-type HMGB1 but does not bind to des-HMGB1 is monoclonal antibody HMa166 produced by a hybridoma identified by accession number NITE BP-02020;

[22] the method of any one of [16] to [21], wherein measuring or detecting total HMGB1 is conducted by an immunological test method;

[23] a kit or reagent for measuring or detecting total HMGB1 in a sample, which comprises the antibodies of (a) and (b) below:
  (a) the antibody of any one of [1] to [7], [9], and [10]; and
  (b) an antibody that binds to both disulfide-type HMGB1 and reduced-type HMGB1 but does not bind to des-HMGB1;

[24] the kit or reagent of [23], wherein total HMGB1 includes disulfide-type HMGB1, reduced-type HMGB1, and thrombin-cleaved HMGB1;

[25] the kit or reagent of [23] or [24], wherein the antibody that binds to both disulfide-type HMGB1 and reduced-type HMGB1 but does not bind to des-HMGB1 is an antibody which recognizes an antigenic determinant comprising the amino acid residues between glycine at position 2 ($G_2$) and alanine at position 17 ($A_{17}$) of disulfide-type HMGB1;

[26-1] the kit or reagent of any one of [23] to [25], wherein the antibody that binds to both disulfide-type HMGB1 and reduced-type HMGB1 but does not bind to des-HMGB1 is an antibody which comprises heavy chain CDR1, CDR2, and CDR3 having the same amino acid sequences as heavy chain CDR1, CDR2, and CDR3 of monoclonal antibody HMa166 produced by a hybridoma identified by accession number NITE BP-02020, and light chain CDR1, CDR2, and CDR3 having the same amino acid sequences as light chain CDR1, CDR2, and CDR3 of monoclonal antibody HMa166 produced by a hybridoma identified by accession number NITE BP-02020;

[26-2] the kit or reagent of any one of [23] to [26-1], wherein the antibody that binds to both disulfide-type HMGB1 and reduced-type HMGB1 but does not bind to des-HMGB1 is an antibody which comprises heavy chain CDR1 having the amino acid sequence of SEQ ID NO: 51, heavy chain CDR2 having the amino acid sequence of SEQ ID NO: 53, and heavy chain CDR3 having the amino acid sequence of SEQ ID NO: 55;

[26-3] the method of any one of [23] to [26-2], wherein the antibody that binds to both disulfide-type HMGB1 and reduced-type HMGB1 but does not bind to des-HMGB1 is an antibody which comprises heavy chain FR1 having the amino acid sequence of SEQ ID NO: 57, heavy chain FR2 having the amino acid sequence of SEQ ID NO: 59, and heavy chain FR3 having the amino acid sequence of SEQ ID NO: 61;

[27-1] the kit or reagent of any one of [23] to [26-3], wherein the antibody that binds to both disulfide-type HMGB1 and reduced-type HMGB1 but does not bind to des-HMGB1 is an antibody which comprises a heavy chain variable region having the same amino acid sequence as the heavy chain variable region of monoclonal antibody HMa166 produced by a hybridoma identified by accession number NITE BP-02020, and a light chain variable region having the same amino acid sequence as the light chain variable region of monoclonal antibody HMa166 produced by a hybridoma identified by accession number NITE BP-02020;

[27-2] the kit or reagent of any one of [23] to [27-1], wherein the antibody that binds to both disulfide-type HMGB1 and reduced-type HMGB1 but does not bind to des-HMGB1 is an antibody which comprises a heavy chain variable region comprising the amino acid sequence of SEQ ID NO: 63 or 74;

[28] the kit or reagent of any one of [23] to [27-2], wherein the antibody that binds to both disulfide-type HMGB1 and reduced-type HMGB1 but does not bind to des-HMGB1 is monoclonal antibody HMa166 produced by a hybridoma identified by accession number NITE BP-02020;

[29] the kit or reagent of any one of [23] to [28], for use in an immunological test method;

[30] an antibody that binds to both disulfide-type HMGB1 and reduced-type HMGB1 but does not bind to des-HMGB1;

[31] the antibody of [30], which recognizes an antigenic determinant comprising the amino acid residues between glycine at position 2 ($G_2$) and alanine at position 17 ($A_{17}$) of disulfide-type HMGB1.

[32-1] the antibody of [30] or [31], which comprises heavy chain CDR1, CDR2, and CDR3 having the same amino acid sequences as heavy chain CDR1, CDR2, and CDR3 of monoclonal antibody HMa166 produced by a hybridoma identified by accession number NITE BP-02020, and light chain CDR1, CDR2, and CDR3 having the same amino acid sequences as light chain CDR1, CDR2, and CDR3 of monoclonal antibody HMa166 produced by a hybridoma identified by accession number NITE BP-02020;

[32-2] the antibody of any one of [30] to [32-1], which comprises heavy chain CDR1 having the amino acid sequence of SEQ ID NO: 51, heavy chain CDR2 having the amino acid sequence of SEQ ID NO: 53, and heavy chain CDR3 having the amino acid sequence of SEQ ID NO: 55;

[32-3] the antibody of any one of [30] to [32-2], wherein the antibody that binds to both disulfide-type HMGB1 and reduced-type HMGB1 but does not bind to des-HMGB1 is an antibody which comprises heavy chain FR1 having the amino acid sequence of SEQ ID NO: 57, heavy chain FR2 having the amino acid sequence of SEQ ID NO: 59, and heavy chain FR3 having the amino acid sequence of SEQ ID NO: 61;

[33-1] the antibody of any one of [30] to [32-3], which comprises a heavy chain variable region having the same amino acid sequence as the heavy chain variable region of monoclonal antibody HMa166 produced by a hybridoma identified by accession number NITE BP-02020, and a light chain variable region having the same amino acid sequence as the light chain variable region of monoclonal antibody HMa166 produced by a hybridoma identified by accession number NITE BP-02020;

[33-2] the antibody of any one of [30] to [33-1], which comprises a heavy chain variable region comprising the amino acid sequence of SEQ ID NO: 63 or 74;

[34] a monoclonal antibody HMa166 produced by a hybridoma identified by accession number NITE BP-02020;

[35] a monoclonal antibody CP11-1 produced by a hybridoma identified by accession number NITE BP-02021.

Effects of the Invention

The present invention provides disulfide-type HMGB1-specific antibodies, methods for specifically measuring or detecting disulfide-type HMGB1 in samples, and kits for specifically measuring or detecting disulfide-type HMGB1 in samples. The present invention also provides methods for measuring or detecting total HMGB1 in samples, and kits for measuring or detecting total HMGB1 in samples. The present invention is useful in the field of life science such as clinical examination, clinical pathology, immunology, and medicine, and particularly to the field of treatment, diagnosis, and research of serious pathological conditions such as inflammation and sepsis. In particular, by specifically measuring or detecting disulfide-type HMGB1, and measuring or detecting the total amount of reduced-type HMGB1, disulfide-type HMGB1, and thrombin-cleaved HMGB1 (des-HMGB1), it is possible to diagnose and analyze the relationship between these HMGB1s and HMGB1-related diseases including sepsis in detail.

BRIEF DESCRIPTION OF THE DRAWINGS

FIG. 2 presents graphs indicating the reactivity between each antibody and the HMGB1 peptides.

FIG. 3 presents graphs indicating the reactivity between each antibody and the HMGB1-NT peptide.

FIG. 14 shows an alignment of the HMa186 $V_H$ region analyzed by IGBLAST.

FIG. 15 shows an alignment of the HMa186 $V_k$ region analyzed by IGBLAST.

FIG. 16 shows an alignment of the HMa166 $V_H$ region analyzed by IGBLAST.

MODE FOR CARRYING OUT THE INVENTION

Figure 1:
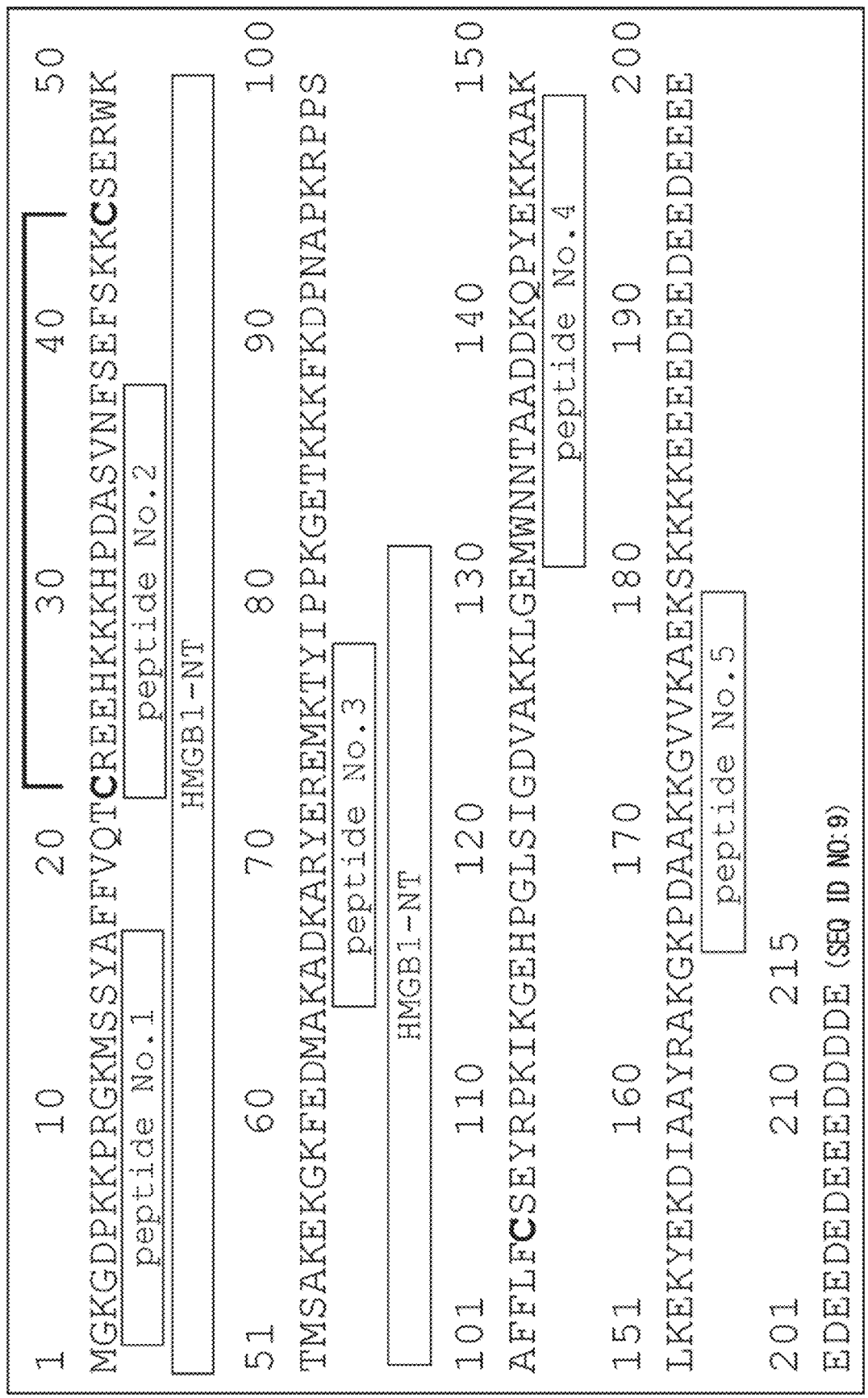
FIG. 1 shows the amino acid sequence (SEQ ID NO: 9) of human HMGB1.

Herein below, the present invention will be described in detail. The following modes for carrying out the invention are only examples and the present invention is not necessarily limited to the following contents.

The present invention relates to an antibody which specifically binds to disulfide-type HMGB1. In the present invention, disulfide-type HMGB1 refers to HMGB1 in which a disulfide bond is formed between cysteines at positions 23 and 45 of HMGB1. Therefore, while the disulfide-type HMGB1-specific antibody of the present invention is not limited to the following, it is preferably an antibody that recognizes an antigenic determinant comprising a disulfide bond formed by cysteines at position 23 ($C_{23}$) and position 45 ($C_{45}$) of disulfide-type HMGB1. Alternatively, while the disulfide-type HMGB1-specific antibody of the present invention is not limited to the following, it is preferably an antibody that recognizes the amino acid sequence consisting of cysteine at position 23 ($C_{23}$) to cysteine at position 45 ($C_{45}$) of disulfide-type HMGB1 as an epitope.

Furthermore, the present invention relates to the antibody which specifically binds to disulfide-type HMGB1, in which the antibody has neutralizing activity against disulfide-type HMGB1 having activity to bind to MD-2 and/or disulfide-type HMGB1 having cytokine-inducing ability. It is known that disulfide-type HMGB1 binds to MD-2 with high affinity in vitro, and promotes the secretion of inflammatory cytokine tumor necrosis factor (TNF) by mouse macrophages. Furthermore, disulfide-type HMGB1 is known to stimulate inflammation (cytokine secretion, and such). Antibodies of the present invention can neutralize such activities possessed by disulfide-type HMGB1. Whether an antibody that binds to disulfide-type HMGB1 neutralizes the activity of disulfide-type HMGB1 can be determined by using a biomolecular interaction analyzer such as Biacore (GE Healthcare) to observe the phenomena of neutralization of this activity by the antibody against disulfide-type HMGB1 bound to MD-2 immobilized onto a sensor chip. Alternatively, the determination can be carried out by adding disulfide-type HMGB1 to immunocompetent cells such as macrophages and established cell lines such as RAW264.7 cells, and measuring the phenomena of neutralization of secretion of cytokines such as TNF, IL-6, IL-10, ILβ, and MIP-2 by the antibody.

Furthermore, the present invention relates to a fragment of the HMGB1 antibody which can specifically recognize disulfide-type HMGB1. Antibody fragments can be generated, for example, by digesting an antibody with an enzyme. Examples of enzymes for generating antibody fragments include papain, pepsin, and plasmin. Alternatively. DNAs encoding such antibody fragments can be constructed, and after inserting them into expression vectors, the antibody fragments can be expressed in appropriate host cells.

The antibody which specifically binds to disulfide-type HMGB1 of the present invention is not particularly limited as long as it can specifically recognize HMGB1 in which a disulfide bond is formed between cysteines at positions 23 and 45 of HMGB1. For example, thrombin-cleaved HMGB1 (des-HMGB1) having the amino acid sequence formed by cleaving off the N-terminal amino acids M1 to R10 of HMGB1 from full-length HMGB1, which is described below, also includes a disulfide bond formed by cysteines at position 23 ($C_{23}$) and position 45 ($C_{45}$) in full-length HMGB1, as with disulfide-type HMGB1. The antibody which specifically binds to disulfide-type HMGB1 of the present invention may also have binding activity to HMGB1 having the amino acid sequence formed by cleaving off the N-terminal amino acids M1 to R10 of HMGB1 from full-length HMGB1, in which a disulfide bond is formed between cysteines at positions 23 and 45 in full-length HMGB1 (or cysteines at positions 13 and 35 in the amino acid sequence formed by cleaving off the N-terminal amino acids M1 to R10 of HMGB1 from full-length HMGB1). The antibody which specifically binds to disulfide-type HMGB1 of the present invention may also be referred to as an antibody specific to an antigenic determinant comprising a disulfide bond formed by cysteines at position 23 ($C_{23}$) and position 45 ($C_{45}$) of HMGB1. Furthermore, the antibody which specifically binds to disulfide-type HMGB1 of the present invention may also be referred to as an antibody specific to an antigenic determinant comprising a disulfide bond formed by cysteines at position 13 ($C_{13}$) and position 35 ($C_{35}$) of thrombin-cleaved HMGB1. That is, the antibody which specifically binds to disulfide-type HMGB1 of the present invention recognizes the disulfide bond of HMGB1.

Furthermore, the present invention relates to low-molecular-weight antibodies (minibodies) of a HMGB1 antibody which can specifically recognize disulfide-type HMGB1. Low-molecular-weight antibodies (minibodies) of the present invention are not particularly limited as long as they include a portion of the whole antibody (antibody fragment) and have an ability to bind to the antigen. Low-molecular-weight antibodies of the present invention preferably include VH (heavy chain variable region) or VL (light chain variable region), and particularly preferably include both VH and VL. Examples of low-molecular-weight antibodies of the present invention include Fab, F(ab')2, Fab', scFv (single-chain Fv), diabody, sc(Fv)2 (single-chain (Fv)2, and such), and their multimers (for example, dimer, trimer, tetramer, and polymer), but are not limited thereto.

An scFv can be obtained by linking the VH and VL of an antibody. In an scFv, VH and VL are linked via a linker or preferably a peptide linker. The peptide linker which links the V regions are not particularly limited. For example, any single-chain peptide consisting of approximately 3 to 25 residues can be used as the linker. A diabody is a dimer composed of two scFvs. An sc(Fv)2 is a low-molecular-weight antibody in which two VHs and two VLs are linked by linkers or such to produce a single chain. An sc(Fv)2 can be prepared, for example, by linking two scFvs with a linker.

Furthermore, the present invention relates to chimeric antibodies, humanized antibodies, and human antibodies of an HMGB1 antibody which can specifically recognize disulfide-type HMGB1.

Chimeric antibodies are antibodies consisting of the variable regions of the heavy and light chains of a non-human mammal antibody such as a mouse antibody, and the constant regions of the heavy and light chains of a human antibody. Chimeric antibodies can be obtained, for example, by obtaining DNAs encoding the variable regions of the heavy and light chains of a HMGB1 antibody which can specifically recognize disulfide-type HMGB1, linking these DNAs with DNAs encoding the constant regions of the heavy and light chains of a human antibody, inserting them into an expression vector, and introducing the vector into a host, and producing the variable regions and constant regions of the antibody heavy and light chains. As the constant regions, constant regions derived from humans, mice, rats, rabbits, dogs, cats, cattle, horses, pigs, goats, rhesus monkeys, cynomolgus monkeys, chimpanzees, chickens, zebrafish, or such can be used. Modifications such as amino acid substitutions, deletions, and additions may be performed on the chimeric antibodies of the present invention to improve the stability of antibody production.

A humanized antibody is an antibody constructed by transferring the complementarity determining regions (CDRs) of an antibody derived from a non-human mammal such as mouse, to the complementarity determining regions of a human antibody. Humanized antibodies can be obtained, for example, by producing a DNA sequence designed to link DNAs encoding the CDRs of the heavy and light chains of a HMGB1 antibody which can specifically recognize disulfide-type HMGB1, and the human antibody framework regions (FR); inserting this into an expression vector; introducing the vector into a host; and expressing the protein encoded by the DNA. Modifications such as amino acid substitutions, deletions, and additions may be performed on the humanized antibodies of the present invention to, e.g., improve the stability of antibody production.

When an amino acid residue is altered, the amino acid is desirably mutated to a different amino acid that conserves the properties of the amino acid side chain. Examples of amino acid side chain properties are as follows: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur atom-containing side chains (C and M), amino acids containing carboxylic acid- and amide-containing side chains (D, N, E, and Q), amino acids containing basic side chains (R, K, and H), and amino acids containing aromatic side chains (H, F, Y, and W). It is already known that a protein containing a modified amino acid sequence in which one or more (for example, 2, 3, 4, 5, 10, 20, 30, 40, 50, or 100) amino acid residues in an amino acid sequence are deleted, added, and/or substituted with other amino acids can retain the original biological activity (Mark, D. F. et al., Proc. Natl. Acad. Sci. USA (1984) 81: 5662-6; Zoller. M. J. and Smith, M., Nucleic Acids Res. (1982) 10: 6487-500; Wang, A. et al., Science (1984) 224: 1431-3; Dalbadie-McFarland, G. et al., Proc. Natl. Acad. Sci. USA (1982) 79: 6409-13). Such mutants have an amino acid identity of at least 70%, more preferably at least 75%, even more preferably at least 80%, still more preferably at least 85%, yet more preferably at least 90%, and most preferably at least 95%, with the amino acid sequence before the amino acid modification. Herein, sequence identity is defined as the proportion of residues identical to those in the original amino acid sequence of the heavy chain variable region or light chain variable region which is determined after the sequences are aligned and gaps are appropriately introduced to maximize the sequence identity as necessary.

The nucleotide sequence or amino acid sequence identity can be determined using the BLAST algorithm by Karlin and Altschul (Proc. Natl. Acad. Sci. USA 87:2264-2268, 1990; and Proc Natl Acad Sci USA 90: 5873, 1993). Programs called BLASTN and BLASTX were developed based on this BLAST algorithm (Altschul S F, et al: J Mol Biol 215: 403, 1990). When analyzing nucleotide sequences using BLASTN, the parameters are set, for example, as score=100 and wordlength=12. On the other hand, parameters used when analyzing amino acid sequences by BLASTX include, for example, score=50 and wordlength=3. Default parameters for each program are used when using the BLAST and Gapped BLAST programs. Specific techniques for such analysis methods are known.

Human antibodies are antibodies prepared from mice which produce human antibodies. Human antibodies can be obtained, for example, by in vitro sensitization of human lymphocytes with desired antigens or cells expressing the desired antigens, and then fusing the sensitized lymphocytes with human myeloma cells such as U266. The human antibodies can also be obtained by immunizing transgenic animals carrying a complete repertoire of human antibody genes with desired antigens.

Furthermore, the present invention relates to an antibody which comprises CDR1, CDR2, and CDR3 having the same amino acid sequences as heavy chain CDR1, CDR2, and CDR3 of monoclonal antibody HMa186, and CDR1, CDR2, and CDR3 having the same amino acid sequences as light chain CDR1, CDR2, and CDR3 of monoclonal antibody HMa186. Antibodies of the present invention may also have FR regions and constant regions.

The amino acid sequences of heavy chain CDR1, CDR2, and CDR3 of monoclonal antibody HMa186 are shown in SEQ ID NOs: 25, 27, and 29, respectively.

The nucleotide sequences of heavy chain CDR1, CDR2, and CDR3 of monoclonal antibody HMa186 are shown in SEQ ID NOs: 24, 26, and 28, respectively.

The amino acid sequences of heavy chain FR1, FR2, and FR3 of monoclonal antibody HMa186 are shown in SEQ ID NOs: 35, 37, and 39, respectively.

The nucleotide sequences of heavy chain FR1, FR2, and FR3 of monoclonal antibody HMa186 are shown in SEQ ID NOs: 34, 36, and 38, respectively.

The amino acid sequences of light chain CDR1 and CDR2 of monoclonal antibody HMa186 are shown in SEQ ID NOs: 31 and 33, respectively.

The nucleotide sequences of light chain CDR1 and CDR2 of monoclonal antibody HMa186 are shown in SEQ ID NOs: 30 and 32, respectively.

The amino acid sequences of light chain FR1, FR2, and FR3 of monoclonal antibody HMa186 are shown in SEQ ID NOs: 41, 43, and 45, respectively.

The nucleotide sequences of light chain FR1, FR2, and FR3 of monoclonal antibody HMa186 are shown in SEQ ID NOs: 40, 42, and 44, respectively.

Such antibodies can be obtained, for example, by the following method. mRNAs encoding the heavy-chain and light-chain CDR1, CDR2, and CDR3 are isolated from hybridomas producing monoclonal antibody HMa186 by a method known to those skilled in the art. Then, the heavy-chain and light-chain CDR1, CDR2, and CDR3 are synthesized from the obtained mRNAs using reverse transcriptase. This is linked with DNAs encoding the desired antibody constant regions and DNAs encoding the FR regions, and this is incorporated into an expression vector. By expressing this expression vector in various expression cells, the antibodies can be collected by methods known to those skilled in the art.

Furthermore, the present invention relates to an antibody which comprises as the heavy chain variable region, a heavy chain variable region having the same amino acid sequence as the heavy chain variable region of monoclonal antibody HMa186; and as the light chain variable region, a light chain variable region having the same amino acid sequence as the light chain variable region of monoclonal antibody HMa186. The antibodies of the present invention may also have constant regions. These antibodies may be obtained by methods such as those described above, which are well-known to those skilled in the art.

The amino acid sequences of the heavy chain variable region and the light chain variable region of monoclonal antibody HMa186 are shown in SEQ ID NOs: 47 and 49, respectively.

The nucleotide sequences of the heavy chain variable region and the light chain variable region of monoclonal antibody HMa186 are shown in SEQ ID NOs: 46 and 48, respectively.

In monoclonal antibody HMa186 of the present invention, one or more (for example, 20 or fewer, 10, 9, 8, 7, 6, 5, 4, 3, 2 or fewer) amino acids may be substituted, deleted, added, and/or inserted.

In the present invention, an example of a HMGB1 antibody that can specifically recognize disulfide-type HMGB1 is monoclonal antibody HMa186. Monoclonal antibody HMa186 is produced by a hybridoma deposited with the Patent Microorganisms Depositary (NPMD) of the National Institute of Technology and Evaluation. The matters specifying the deposit are described below.

(1) Depositary institution: The National Institute of Technology and Evaluation (2) Contact information: 2-5-8, Kazusakamatari, Kisarazu-city, Chiba, 292-0818, Japan (3) Accession No.: NITE BP-02019

(4) Indication for identification: HMa186

(5) Date of national deposit: Mar. 5, 2015

(6) Date of request for transfer to international depositary: Nov. 4, 2016

Furthermore, the present invention relates to specifically measuring or detecting disulfide-type HMGB1 in a sample, which comprises the step of contacting the sample with the antibody which specifically binds to disulfide-type HMGB1 of the present invention.

Furthermore, the present invention relates to a method for measuring or detecting total HMGB1 in a sample, which comprises contacting the sample with the antibodies of (a) and (b) below:

(a) an antibody which specifically binds to disulfide-type HMGB1 and (b) an antibody that binds to both disulfide-type HMGB1 and reduced-type HMGB1 but does not bind to thrombin-cleaved HMGB1 (des-HMGB1).

Furthermore, the present invention relates to an antibody that binds to both disulfide-type HMGB1 and reduced-type HMGB1 but does not bind to thrombin-cleaved HMGB1 (des-HMGB1).

The antibody which specifically binds to disulfide-type HMGB1 of the present invention can recognize thrombin-cleaved HMGB1 (des-HMGB1) which has an amino acid sequence produced by cleaving off the N-terminal amino acids M1 to R10 of full-length HMGB1. This is because even after disulfide-type HMGB1 is cleaved by thrombin to form thrombin-cleaved HMGB1, the disulfide bond is maintained between the cysteines of positions 13 and 35 of thrombin-cleaved HMGB1 which correspond to cysteines at positions 23 and 45 of full-length HMGB1.

"Total HMGB1" of the present invention includes those formed by subjecting the amino acid sequence of HMGB1 to alteration (addition, deletion, insertion, substitution, and such), chemical modification, or enzymatic treatment. More specifically, examples include, but are not limited to, disulfide-type HMGB1, reduced-type HMGB1, and thrombin-cleaved HMGB1, and those formed by subjecting them to amino acid alteration, chemical modification, enzymatic treatment, and such.

Furthermore, in the present invention, reduced-type HMGB1 refers to HMGB1 in a condition where all three cysteines ($C_{23}$, $C_{45}$, and $C_{106}$) are reduced. It is known that it involves in regulating genetic information in the cell nucleus, and has chemotaxis (chemotaxis-inducing) activity outside the cell.

Thrombin-cleaved HMGB1 (des-HMGB1) refers to a cleavage product of HMGB1 having a newly generated N-terminal "GKMSS . . . " (SEQ IS NO: 76) which is formed by cleavage between arginine at position 10 ($R_{10}$) and glycine at position 11 ($G_{11}$) of HMGB1 by thrombin or a thrombin/thrombomodulin complex, and separation of a peptide fragment composed of N-terminal ten amino acid residues of HMGB1. This cleavage product of HMGB1 is known to have lower biological activity than HMGB1. Thrombin-cleaved HMGB1 has a disulfide bond between the cysteines at positions 13 and 35 which correspond to cysteines at positions 23 and 45 of full-length HMGB1. In the present invention, disulfide-type HMGB1 and thrombin-cleaved HMGB1 which maintains the disulfide bond can be collectively referred to as non-reduced-type HMGB1 or disulfide bond-containing HMGB1. Furthermore, in the present invention, "antibody which specifically binds to disulfide-type HMGB1" can be referred to as "antibody which specifically binds to non-reduced-type HMGB1" or "antibody which specifically binds to HMGB1 having a disulfide bond".

In the present invention, the antibody that binds to both disulfide-type HMGB1 and reduced-type HMGB1 but does not bind to des-HMGB1 is, for example, an antibody which recognizes an antigenic determinant comprising the amino acid residues between glycine at position 2 ($G_2$) and alanine at position 17 ($A_{17}$) of disulfide-type HMGB1, but it is not limited thereto. Alternatively, the antibody of the present invention may be, for example, an antibody that recognizes an amino acid sequence consisting of the amino acid residues between glycine at position 2 ($G_2$) and alanine at position 17 ($A_{17}$) of disulfide-type HMGB1 as the epitope, but it is not limited thereto.

Furthermore, in the present invention, an example of the antibody that binds to both disulfide-type HMGB1 and reduced-type HMGB1 but does not bind to des-HMGB1 is an antibody which comprises CDR1, CDR2, and CDR3 having the same amino acid sequences as heavy chain CDR1, CDR2, and CDR3 of monoclonal antibody HMa166, and CDR1, CDR2, and CDR3 having the same amino acid sequences as light chain CDR1, CDR2, and CDR3 of monoclonal antibody HMa166, but is not limited thereto. Such antibodies may also have FR regions and constant regions.

The amino acid sequences of heavy chain CDR1, CDR2, and CDR3 of monoclonal antibody HMa166 are shown in SEQ ID NOs: 51, 53, and 55, respectively.

The nucleotide sequences of heavy chain CDR1, CDR2, and CDR3 of monoclonal antibody HMa166 are shown in SEQ ID NOs: 50, 52, and 54, respectively.

The amino acid sequences of heavy chain FR1, FR2, and FR3 of monoclonal antibody HMa166 are shown in SEQ ID NOs: 57, 59, and 61, respectively.

The nucleotide sequences of heavy chain FR1, FR2, and FR3 of monoclonal antibody HMa166 are shown in SEQ ID NOs: 56, 58, and 60, respectively.

Furthermore, in the present invention, the antibody that binds to both disulfide-type HMGB1 and reduced-type HMGB1 but does not bind to des-HMGB1 relates to an antibody which has as the heavy chain variable region, a variable region having the same amino acid sequence as the heavy chain variable region of monoclonal antibody HMa166; and as the light chain variable region, a light chain variable region having the same amino acid sequence as the light chain variable region of monoclonal antibody HMa166. Such antibodies may also have constant regions.

The amino acid sequence of the heavy chain variable region of monoclonal antibody HMa166 is shown in SEQ ID NO: 63.

The nucleotide sequence of the heavy chain variable region of monoclonal antibody HMa166 is shown in SEQ ID NO: 62.

These antibodies can be obtained by methods well-known to those skilled in the art, such as those described above.

In monoclonal antibody HMa166 of the present invention, one or more (for example, 20 or fewer, 10, 9, 8, 7, 6, 5, 4, 3, 2 or fewer) amino acids are substituted, deleted, added, and/or inserted.

In the present invention, an example of an antibody that binds to both disulfide-type HMGB1 and reduced-type HMGB1 but does not bind to des-HMGB1 is monoclonal antibody HMa166. Monoclonal antibody HMa166 is produced by a hybridoma deposited with the Patent Microorganisms Depositary of the National Institute of Technology and Evaluation. The matters specifying the deposit are described below.

(1) Depositary institution: The National Institute of Technology and Evaluation (2) Contact information: 2-5-8, Kazusakamatari, Kisarazu-city, Chiba, 292-0818, Japan (3) Accession No.: NITE BP-02020

(4) Indication for identification: HMa166

(5) Date of national deposit: Mar. 5, 2015

(6) Date of request for transfer to international depositary: Nov. 4, 2016

Furthermore, the present invention relates to a kit or reagent for use in a method mentioned above. The kit or reagent of the present invention relates to a kit or reagent for specifically measuring or detecting disulfide-type HMGB1 contained in a sample, where the kit or reagent contains at least the antibodies that specifically bind to disulfide-type HMGB1 of (a) and (b) below. Furthermore, the kit or reagent of the present invention relates to a kit or reagent for measuring or detecting total HMGB1 in a sample, which comprises at least the antibodies of (a) and (b) below:

(a) an antibody which specifically binds to disulfide-type HMGB1; and (b) an antibody that binds to both disulfide-type HMGB1 and reduced-type HMGB1 but does not bind to thrombin-cleaved HMGB1 (des-HMGB1).

In the present invention, the types, origins, and such of the HMGB1 antibodies (for example, antibodies that specifically bind to disulfide-type HMGB1, and antibodies that bind to both disulfide-type HMGB1 and reduced-type HMGB1 but does not bind to des-HMGB1) are not limited. Examples include antibodies obtained from various immunized animals such as mice, rabbits, and goats. Furthermore, polyclonal antibodies, antiserum containing polyclonal antibodies, monoclonal antibodies, or antibody fragments thereof (for example, Fab, F(ab')2, and Fab'), low-molecular-weight antibodies (minibodies) (for example, single-chain Fv (scFv), diabody, and single-chain (Fv)2 (sc(Fv)2)), and their multimers (for example, dimers, trimers, tetramers, and polymers) may also be used.

For example, polyclonal antibodies can be prepared by immunizing an animal such as rabbit with purified HMGB1 (disulfide-type HMGB1, reduced-type HMGB1, or such) or a partial peptide thereof, collecting the blood after a certain period of time, and then removing blood clots. On the other hand, monoclonal antibodies can be prepared by fusing bone tumor cells with antibody producing cells from an animal immunized with HMGB1 or a partial peptide thereof, isolating cells from a single clone that produces the antibody of interest (hybridoma), and obtaining antibodies from the cells.

The origin of HMGB1 is not limited in the present invention. In the present invention, without limitation, HMGB1 derived from humans, mice, rats, rabbits, dogs, cats, cattle, horses, pigs, goats, rhesus monkeys, cynomolgus monkeys, chimpanzees, chickens, zebrafish, or such can be measured or detected.

The NCBI (National Center for Biotechnology Information, U.S. National Library of Medicine) database accession numbers and the SEQ ID NOs used herein are shown below for the amino acid sequences of HMGB1 derived from various animals:

```
human [Homo sapiens] CAG33144.1/SEQ ID NO: 9
mouse [Mus musculus] AAI10668.1/SEQ ID NO: 10
rat [Rattus norvegicus] NP_037095.1/SEQ ID NO: 11
rabbit [Oryctolagus cuniculus] NP_001164752.1/SEQ ID NO: 12
dog [Canis lupus familiaris] AAN11319.1/SEQ ID NO: 13
cat [Felis catus] XP_006927254.1/SEQ ID NO: 14
cattle [Bos taurus] AAI02930.1/SEQ ID NO: 15
horse [Equus caballus] BAF33339.1/SEQ ID NO: 16
pig [Sus scrofa] NP_001004034.1/SEQ ID NO: 17
goat [Capra hircus] XP_005687595.1/SEQ ID NO: 18
rhesus monkey [Macaca mulatta] AFJ72047.1/SEQ ID NO: 19
cynomolgus monkey [Macaca fascicularis] NP_001270285.1/SEQ ID NO: 20
chimpanzee [Pan troglodytes] XP_509611.1/SEQ ID NO: 21
chicken [Gallus gallus] NP_990233.1/SEQ ID NO: 22
zebrafish [Danio rerio] AAH67193.1/SEQ ID NO: 23
```

In the present invention, samples refer to solutions which contain or are suspected to contain HMGB1 (e.g., disulfide-type HMGB1, reduced-type HMGB1, and thrombin-cleaved HMGB1). Examples include isolated biological samples such as blood, serum, plasma, urine, semen, spinal fluid, saliva, sweat, tear, ascites, and amniotic fluid derived from humans or other animals, for example, mice, rats, rabbits, dogs, cats, bovines, horses, pigs, goats, sheep, monkeys (for example, rhesus monkeys and cynomolgus monkeys), chimpanzees, chickens, and zebrafish; and diluted solutions containing them, but are not limited thereto. Furthermore, solutions obtained by mixing solutions which contain or are suspected to contain HMGB1 with buffers and such are also included in the samples of the present invention. Methods of obtaining such samples are well known to those skilled in the art. Various aqueous solvents can be used as the solvents for mixing or dilution. Examples include purified water, physiological saline solution, or various buffers such as Tris buffer, phosphate buffer, or phosphate buffered saline solution, but are not limited thereto. Furthermore, pH of the buffers is not particularly limited, and suitable pH can be appropriately selected. Generally, pH in the range of pH 3 to 12 can be selected and used, but is not limited thereto. Furthermore, for structural protection of substances to be measured, the solvents may appropriately contain one, two or more kinds of proteins such as bovine serum albumin (BSA), human serum albumin (HSA), and casein; various saccharides; powdered skimmed milk; various animal sera such as normal rabbit serum; various antiseptics such as sodium azide and antibiotics; and various surfactants such as nonionic surfactants, amphoteric surfactants, and anionic surfactants.

The means for contacting a sample with a HMGB1 antibody (an antibody which specifically binds to disulfide-type HMGB1, an antibody that binds to both disulfide-type HMGB1 and reduced-type HMGB1 but does not bind to des-HMGB1, or such) is not particularly limited. More specifically, a HMGB1 antibody can be added to a container in which a sample is contained. Alternatively, a sample can be added to a container in which a HMGB1 antibody is contained.

In the present invention, known techniques can be used for measuring or detecting HMGB1 (for example, disulfide-type HMGB1, and total HMGB1). Examples include immunological testing methods such as enzyme-linked immunosorbent assay (ELISA, EIA), fluoroimmunoassay (FIA), Western blotting, dot blotting, immunoprecipitation methods, radioimmunoassay (RIA), luminescent immunoassay (LIA), immunoenzyme technique, fluorescent antibody technique, immunochromatography method, immunonephelometry, latex turbidimetry, and latex agglutination assay, but are not limited thereto. Furthermore, measurement or detection in the present invention may be performed manually or by using an apparatus such as an analyzer.

For example, when using enzyme immunoassay, it can be performed using a microplate on which a first HMGB1 antibody (an antibody which specifically binds to disulfide-type HMGB1, an antibody that binds to both disulfide-type HMGB1 and reduced-type HMGB1 but does not bind to des-HMGB1, or such) is immobilized, a second HMGB1 antibody modified with an enzyme such as HRP, a washing buffer, a luminescentichromogenic substrate solution, a standard substance (human recombinant HMGB1), a positive control (human recombinant HMGB1), a sample diluent, a reaction-stopping solution, and such. Furthermore, HMGB1 can be measured or detected by reacting an enzyme used to modify the second HMGB1 antibody with a substrate of this enzyme under optimal conditions, and measuring the amount of the enzyme reaction products by optical methods. The second HMGB1 antibody (detection antibody) is preferably an antibody that recognizes an epitope that is different from the epitope recognized by the first HMGB1 antibody (immobilized antibody).

Alternatively, when using fluoroimmunoassay, measurement or detection can be performed using an optical waveguide or a microplate onto which a first HMGB1 antibody is immobilized, a second HMGB1 antibody modified with a fluorescent substance, and washing buffers. Measurement or detection of HMGB1 can be carried out by applying excitation light to the fluorescent substance used to modify the second HMGB1 antibody, and measuring the intensity of the fluorescence emitted by the fluorescent substance. Furthermore, when using radioimmunoassay, HMGB1 can be measured or detected by measuring radiation quantity from a radioactive substance by operations similar to those of the method described above, and when using luminescent immunoassay, HMGB1 can be measured or detected by measuring the amount of luminescence from luminescent reaction systems.

When using western blotting or dot blotting methods, after electrophoresis, transfer membranes or membranes to which samples are directly applied are subjected to blocking with BSA or skimmed milk, and then measurement or detection can be performed using an HMGB1 antibody modified with an enzyme such as HRP, washing buffers, and luminescenti chromogenic substrate solutions, etc. A secondary antibody directly labeled with an enzyme, a fluorescent dye, or such may be reacted with a first HMGB1 antibody.

HMGB1 can be measured or detected by reacting the above-mentioned substrate with an enzyme used to modify the HMGB1 antibody or the secondary antibody under appropriate conditions, and measuring the amount of products of the enzymatic reaction by optical methods.

When using immunoprecipitation, blocking agents such as BSA or skimmed milk can be added during reaction of samples with the HMGB1 antibodies and the like. Precipitation is carried out using magnetic beads, agarose substrates, or such directly bound to HMGB1 antibodies, or by using secondary antibodies bound to those beads and such.

Furthermore, when using immunoturbidimetry, a latex turbidimetry, a latex agglutination assay, or the like, HMGB1 can be measured or detected by measuring the transmitted light and the scattered light by an endpoint method or rate method. Also, when immunochromatography is used, the color of labeled substances appearing on the test line can be visually identified. Moreover, instruments such as an analyzer can be used instead of the visual identification.

As the solid-phase carriers to be used in the above immunological assays, solid-phase carriers in the form of beads, microplates, test tubes, sticks, membranes, specimen pieces, or the like made of materials such as polystyrene, polycarbonate, polyvinyl toluene, polypropylene, polyethylene, polyvinyl chloride, nylon, polymethacrylate, polyacrylamide, latex, a liposome, gelatin, agarose, cellulose, sepharose, glass, metal, ceramic, or magnetic material can be used, but are not limited thereto.

As methods for immobilization of HMGB1 antibodies mentioned above on a solid phase, known immobilization methods may be used. For example, methods for physical adsorption include methods of mixing antibodies and carriers in solutions such as buffers to contact them, or methods of contacting carriers with antibodies dissolved in buffers or such, but are not limited thereto.

Furthermore, when immobilizing HMGB1 antibodies by chemical bonding methods, preparations can also be performed according to known methods. Examples of such methods include a method in which the antibodies and carriers are mixed with divalent cross-linking reagents such as glutaraldehyde, carbodiimide, imide ester, or maleimide and contacted with each other to react amino groups, carboxyl groups, thiol groups, aldehyde groups, hydroxyl groups, or the like of both the antibodies and the carriers, but are not limited thereto.

Furthermore, if it is necessary to perform treatments for suppressing non-specific reactions, spontaneous aggregation of the carriers onto which the HMGB1 antibodies are immobilized, and the like, such treatments can be performed according to known methods. Examples of such methods include a method in which the antibody-immobilized surface or inner wall of the carriers is contacted with proteins such as bovine serum albumin (BSA), casein, gelatin, ovalbumin. or salts thereof, surfactants, powdered skimmed milk, or the like to coat the surface or the inner wall of the carriers, but are not limited thereto.

Known modification methods can be used as the method for modifying the above-mentioned second HMGB1 antibody with labeling substances. Examples of physical adsorption methods include, but are not limited to, a method in which the second HMGB1 antibody and labeling substances are mixed and contacted with each other in solutions such as buffers and a method in which the antibody dissolved in buffers and the like is contacted with labeling substances. For example, when the labeling substance is gold colloid or latex, physical adsorption methods are effective. Antibodies labeled with gold colloid can be obtained by mixing the antibodies and gold colloid in buffers to contact them with each other.

Furthermore, when modifying the second HMGB1 antibody with labeling substances by chemical bonding methods, the preparation can be carried out according to known methods. Examples of such methods include, but are not limited to, a method in which the antibody and labeling substances are mixed with divalent cross-linking reagents such as glutaraldehyde, carbodiimide, imide ester, or maleimide and contacted with each other to react amino groups, carboxyl groups, thiol groups, aldehyde groups, hydroxyl groups, or the like of both the antibody and the labeling substances. For example, when the labeling substance is a fluorescent substance, an enzyme, or a chemiluminescent substance, a chemical bonding method is effective.

Furthermore, if it is necessary to perform treatments for suppressing non-specific reactions, spontaneous aggregation of the antibody modified with labeling substances, and the like, such treatments can be performed according to known methods. Examples of such methods include, but are not limited to, a method in which the antibodies conjugated with labeling substances are contacted with proteins such as bovine serum albumin (BSA), casein, gelatin, ovalbumin, or salts thereof, surfactants, powdered skimmed milk, or the like to coat the antibodies.

For labeling substances, when an enzyme immunoassay is carried out, without being limited to the following, peroxidase (POD), alkaline phosphatase (ALP), β-galactosidase, urease, catalase, glucose oxidase, lactate dehydrogenase, amylase, or the like can be used.

When a fluorescent immunoassay is carried out, without being limited to the following, fluorescein isothiocyanate, tetramethylrhodamine isothiocyanate, substituted rhodamine isothiocyanate, dichlorotriazine isothiocyanate, cyanine, merocyanine, or the like can be used.

When a radioimmunoassay is carried out, without being limited to the following, tritium, iodine-125, iodine-131, or the like can be used.

When a luminescence immunoassay is carried out, without being limited to the following, luminol compounds, luciferase compounds, acridinium esters, dioxetane compounds, or the like can be used.

When immunochromatography, immunoturbidimetry, latex turbidimetry, and latex agglutination assay are carried out, without being limited to the following, particles can be used, which are made of materials such as polystyrene, styrene-styrene sulfonate copolymer, acrylonitrile-butadiene-styrene copolymer, vinyl chloride-acrylic acid ester copolymer, vinyl acetate-acrylic acid copolymer, polyacrolein, styrene-methacrylic acid copolymer, styrene-glycidyl (meth)acrylic acid copolymer, styrene-butadiene acid copolymer, methacrylic acid polymer, acrylic acid polymer, latex, gelatin, liposome, microcapsule, silica, alumina, carbon black, metal compound, metal, metal colloid, ceramic, or magnetic material.

The kits or reagents of the present invention are characterized in that they are used by contacting the HMGB1 antibody with a sample. The kits or reagents of the present invention are not particularly limited so long as they are constituted so that HMGB1 in a sample (for example, disulfide-type HMGB1, reduced-type HMGB1, or thrombin-cleaved HMGB1) binds to a HMGB1 antibody (for example, an antibody which specifically binds to disulfide-type HMGB1, or an antibody that binds to both disulfide-type HMGB1 and reduced-type HMGB1 but does not bind to des-HMGB1).

For the constitution of the kits of the present invention, substances may be combined with other reagents or they can be adhered to solid phases in advance. For example, when combined in advance with other reagents, the reagents to be combined include buffers necessary for binding between HMGB1 in the samples and the HMGB1 antibodies, sample dilution solutions, solutions of HMGB1 antibodies containing labeling substances such as an enzyme, reagents containing substances that generate a signal such as color development, reagents containing substances involved in generation of a signal such as color development, reagents containing substances for calibration, and reagents containing substances used for accuracy control. Examples of the solid phase include carriers and test papers to be used in the immunological testing kits, microplates, glass plates, microtubes, filter papers, and polymer resins.

The kits or reagents of the present invention include materials that are necessary for measuring or detecting HMGB1. Kits or reagents of the present invention also include a kit or reagent including various sets necessary for measuring or detecting HMGB1, a disposable kit or reagent which contains various substances necessary for measuring or detecting HMGB1, a microplate-type testing kit or reagent for simultaneously measuring multiple samples, and test paper or immunochromatography that contains reagents and such and allows determination of results by visual observation.

As an example of the form of a disposable kit or reagent, one can consider a constitution where a spherical or rod-shaped carrier on which the first HMGB1 antibody is immobilized, a reagent dilution solution, a second HMGB1 antibody modified with an enzyme such as ALP, a washing solution, a luminescent substrate solution, a standard substance (human recombinant HMGB1), a positive control (human recombinant HMGB1), a sample dilution solution, a reaction-stopping solution, and such are contained in a testing container, but it is not limited thereto.

The form of the testing containers is not particularly limited as long as HMGB1 in the samples can be measured or detected. Examples include, but are not limited to, boat-shaped containers in which multiple reaction chambers and reagent storage chambers are aligned, and flow-channel-type containers in which grooves are provided on a sheet-type substrate and reaction chambers and storage chambers are connected by flow channels. Furthermore, while the size of the testing container is not particularly limited, but for use by incorporation into an automated analyzer and such, a small size such as approximately 10 cm×10 cm or smaller is desired. Furthermore, to avoid intrusion of foreign matter into the reaction chambers and evaporation/deterioration of reagents packed in the reagent storage chambers, the upper portion of each chamber may be sealed. Examples include a method of adhesion of aluminum foil, polymeric film, or such to the upper portion of the reaction chambers and storage chambers of the testing container. In particular, sealing with aluminum foil is preferred since it can be easily opened using the tip of a dispenser chip or the punching structure of an analyzer. The material for the testing container is not particularly limited as long as it does not inhibit the reaction for measuring the substances to be measured. Examples include, but are not limited to, polystyrene resins, polyethylene resins, and polypropylene resins.

Furthermore, the following constitution can be considered as a form of the microplate-type kit or reagent. For example, a sample dilution solution, a second HMGB1 antibody modified with an enzyme such as HRP, a washing solution, a chromogenic substrate solution, a standard substance (human recombinant HMGB1), a positive control (human recombinant HMGB1), a sample dilution solution, a reaction-stopping solution, and such are respectively provided in reagent bottles and they are included with a microplate to which the first HMGB1 antibody is immobilized.

A suitable form of immunochromatography is lateral flow composed of a housing case, sample pad, conjugation pad, membrane filter, and absorption pad. Lateral flow is prepared by the following procedure. First, a first HMGB1 antibody labeled with gold colloid or colored beads is prepared, and this is applied to the conjugation pad, and this is dried. On the other hand, a second HMGB1 antibody is applied on the test line of the membrane filter, and this is dried. Next, a third antibody that specifically recognizes the second HMGB1 antibody is applied on the control line of the membrane filter, and this is dried. Finally, the above-mentioned conjugation pad, sample pad, and absorption pad are attached to this filter to provide the lateral flow.

In the present invention, the forms of the reagents are not particularly limited and may be solutions containing the HMGB1 antibody. Alternatively, they may have volumes and forms in accordance with the test of interest; for example, they are tablets or powders, or in dry forms adhered to containers.

The kits or reagents of the present invention may be kits or reagents for sandwich ELISA which comprise a labeled antibody for detection and the antibody which specifically binds to disulfide-type HMGB1 of the present invention. In particular, when measuring or detecting total HMGB1 including disulfide-type HMGB1, reduced-type HMGB1, and thrombin-cleaved HMGB1, in one embodiment, this can be performed by sandwich ELISA which uses monoclonal antibodies HMa166 and HMa186 as the solid-phase antibodies, and monoclonal antibody CP11-1 as the detection antibody. Monoclonal antibody CP11-1 is produced by a hybridoma deposited with the Patent Microorganisms Depositary (NPMD) of the National Institute of Technology and Evaluation. The matters specifying the deposit are described below.

(1) Depositary institution: The National Institute of Technology and Evaluation (2) Contact information: 2-5-8, Kazusakamatari, Kisarazu-city, Chiba, 292-0818, Japan (3) Accession No.: NITE BP-02021

(4) Indication for identification: CP11-1

(5) Date of national deposit: Mar. 5, 2015

(6) Date of request for transfer to international depositary: Nov. 4, 2016

Furthermore, the present invention relates to methods for diagnosing sepsis or sepsis-related diseases such as systemic inflammation, which comprise the step of measuring or detecting HMGB1 (disulfide-type HMGB1 or total HMGB1) in a sample using the measurement or detection method of the present invention.

Furthermore, the present invention relates to kits or reagents for diagnosing sepsis or sepsis-related diseases such as systemic inflammation, which comprise a disulfide-type HMGB1-specific antibody or an antibody that binds to both disulfide-type HMGB1 and reduced-type HMGB1 but does not bind to des-HMGB1.

In the diagnosis methods, and kits or reagents for diagnosis of the present invention, for example, when disulfide-type HMGB1 is detected, a subject is determined to be suffering from sepsis or a sepsis-related disease. The present invention may comprise a step of administering a known therapeutic agent for sepsis or a sepsis-related disease to or performing a known therapeutic method on a subject in which HMGB1 was detected.

While further future research is necessary regarding the correlation between blood HMGB1 concentration and the severity of sepsis and sepsis-related diseases, it is known that blood concentration of HMGB1 is high in sepsis patients (Wang, SCIENCE, 285, 248-251, 1999). Furthermore, it has been reported that blood HMGB1 concentration and diagnostic criteria for sepsis such as SOFA score, lactate level, and procalcitonin level are highly correlated (Gibot, Intensive Care Medicine, 33, 1347-1353, 2007). Furthermore, it has been reported that after onset of sepsis, the blood concentration of disulfide-type HMGB1 decreased with passage of time in patients who did not die, but the blood concentration of disulfide-type HMGB1 increased with passage of time in patients with poor prognosis or died after onset of the disease (Gibot, Intensive Care Medicine, 33, 1347-1353, 2007). Furthermore, there is a report of treated cases where blood purifying treatment was performed on sepsis patients, and elevated HMGB1 concentrations recovered to normal levels, and finally discharge from the hospital was achieved (Nakamura, Blood Purification, 32, 139-142, 2011). Thus, blood HMGB1 concentration can serve as important information for initiation of and withdrawal from various treatments.

The relationship between the sequences of monoclonal antibodies HMa186 and HMa166 and the SEQ ID NOs shown in the Sequence Listing is summarized below.

Monoclonal antibody HMa186:
  Heavy chain CDR1 nucleotide sequence: SEQ ID NO: 24
  Heavy chain CDR1 amino acid sequence: SEQ ID NO: 25
  Heavy chain CDR2 nucleotide sequence: SEQ ID NO: 26
  Heavy chain CDR2 amino acid sequence: SEQ ID NO: 27
  Heavy chain CDR3 nucleotide sequence: SEQ ID NO: 28
  Heavy chain CDR3 amino acid sequence: SEQ ID NO: 29
  Light chain CDR1 nucleotide sequence: SEQ ID NO: 30
  Light chain CDR1 amino acid sequence: SEQ ID NO: 31
  Light chain CDR2 nucleotide sequence: SEQ ID NO: 32
  Light chain CDR2 amino acid sequence: SEQ ID NO: 33
  Heavy chain FR1 nucleotide sequence: SEQ ID NO: 34
  Heavy chain FR1 amino acid sequence: SEQ ID NO: 35
  Heavy chain FR2 nucleotide sequence: SEQ ID NO: 36
  Heavy chain FR2 amino acid sequence: SEQ ID NO: 37
  Heavy chain FR3 nucleotide sequence: SEQ ID NO: 38
  Heavy chain FR3 amino acid sequence: SEQ ID NO: 39
  Light chain FR1 nucleotide sequence: SEQ ID NO: 40
  Light chain FR1 amino acid sequence: SEQ ID NO: 41
  Light chain FR2 nucleotide sequence: SEQ ID NO: 42
  Light chain FR2 amino acid sequence: SEQ ID NO: 43
  Light chain FR3 nucleotide sequence: SEQ ID NO: 44
  Light chain FR3 amino acid sequence: SEQ ID NO: 45
  Heavy chain variable region nucleotide sequence: SEQ ID NO: 46
  Heavy chain variable region amino acid sequence: SEQ ID NO: 47
  Light chain variable region nucleotide sequence: SEQ ID NO: 48
  Light chain variable region amino acid sequence: SEQ ID NO: 49

Monoclonal antibody HMa166:
  Heavy chain CDR1 nucleotide sequence: SEQ ID NO: 50
  Heavy chain CDR1 amino acid sequence: SEQ ID NO: 51
  Heavy chain CDR2 nucleotide sequence: SEQ ID NO: 52
  Heavy chain CDR2 amino acid sequence: SEQ ID NO: 53
  Heavy chain CDR3 nucleotide sequence: SEQ ID NO: 54
  Heavy chain CDR3 amino acid sequence: SEQ ID NO: 55
  Heavy chain FR1 nucleotide sequence: SEQ ID NO: 56
  Heavy chain FR1 amino acid sequence: SEQ ID NO: 57
  Heavy chain FR2 nucleotide sequence: SEQ ID NO: 58
  Heavy chain FR2 amino acid sequence: SEQ ID NO: 59
  Heavy chain FR3 nucleotide sequence: SEQ ID NO: 60
  Heavy chain FR3 amino acid sequence: SEQ ID NO: 61
  Heavy chain variable region nucleotide sequence: SEQ ID NO: 62
  Heavy chain variable region amino acid sequence: SEQ ID NO: 63

All prior art references cited herein are incorporated by reference into this description.

EXAMPLES

Herein below, the present invention will be specifically described with reference to the Examples, but it is not to be construed as being limited thereto.

1. Preparation of *Escherichia coli* (*E. coli*) Recombinant Human HMGB1

The method for preparing recombinant human HMGB1 using *E. coli* is indicated below.

A gene having an upstream restriction enzyme site NdeI and a downstream restriction enzyme site BamHI for cloning added to the human HMBG1 gene sequence registered in GenBank (GenBank: CR456863.1/SEQ ID NO: 7) was prepared by chemical synthesis. The synthesized human HMGB1 gene was ligated to the pET15b plasmid vector which can add a histidine tag at the N-terminus, and after sequence confirmation, this was used to transform *E. coli* BL21 (DE3). The HMGB1-NT gene which encodes human HMGB1 from its N terminus to lysine at position 82 (M1-K82) was prepared similarly.

*E. coli* BL21(DE3) (HMGB1/pET15b) (i.e., *E. coli* BL21 (DE3) into which the obtained human HMGB1 gene was transferred) and *E. coli* BL21(DE3) (HMGB1-NT/pET15b) were individually cultured in approximately 2 L of *E. coli* culture medium such as Circle Grow (Funakoshi) or 2× YT (DIFCO). When the turbidity ($OD_{600\ nm}$) reached around 0.5, 0.5 mM IPTG was added for induction at 30° C. for three hours to express the recombinant human HMGB1 proteins.

*E. coli* BL21(DE3) (HMGB1/pET15b) and *E. coli* BL21 (DE3)(HMGB1-NT/pET15b) cells with the expression were collected by centrifugation, and they were rapidly frozen at −80° C., and then the cells were suspended by adding 20 mM Tris-HCl (pH7.5), 0.5 M NaCl. and 1% Triton X-100. The suspension was placed on ice, and the bacterial cells were disrupted using a sonicator.

Thereafter, centrifugation was performed, and supernatants of the disrupted cells were sterilized by filtration through 0.22-μm filters for filter sterilization.

To the filtered disrupted cell supernatant, 50 mM imidazole was added, and this was applied to 5-mL HisTrap HP column (GE Healthcare) for purification using the histidine tag. After washing, elution was conducted stepwise using 75 mM, 100 mM, and 500 mM imidazole. The fractions found to have the proteins of interest were subjected to buffer exchange with 10 mM sodium phosphate buffer (pH7.0), then this was applied to histidine tag HiTrap Heparin HP 1-mL column (GE Healthcare) and eluted using linear gradient of NaCl from 50 mM to 1100 mM.

The fractions found to have the proteins of interest were subjected to five-fold dilution using 10 mM Hepes, and this was applied to Hitrap CMFF column (GE Healthcare), and then eluted using linear gradient of NaCl from 0 mM to 180 mM. The fractions found to have the proteins of interest were concentrated using ultrafiltration membranes, and this was subjected to buffer exchange using 50 mM Hepes (pH8.0) in 500 mM NaCl, and then purified.

2. Preparation of Monoclonal Antibodies
(1) Method of Producing Monoclonal Antibody CP11-1

A hapten-carrier protein complex was prepared by adding a cysteine (C) to the C terminus of the peptide No. 5 of positions 167 to 180 (KPDAAKKGVVKAEK/SEQ ID NO: 6) in the amino acid sequence of human HMGB1, which was used as a hapten, and linking it via the SH group of the cysteine to keyhole limpet hemocyanin (KLH) which is a carrier. Initial immunization of mice (Balb/c) was carried out using 100 μg of the prepared hapten-carrier protein complex antigen together with Freund's complete adjuvant (FCA), and 14 days later, as a booster, the mice were immunized with 50 μg of the hapten-carrier protein complex, which was used for the initial immunization, together with Freund's incomplete adjuvant (FIA). Thereafter, with 14-day intervals, immunization was carried out four times in total using 50 μg of the hapten-carrier protein complex with FIA. After the final immunization, the spleen was removed, and lymphocytes were prepared according to a standard method and fused with myeloma Sp2/0-Ag14 (ATCC: CRL-1581). The hybridomas resulting from the fusion were cultured and cloned using a ClonaCell-HY Hybridoma Cloning Kit (STEM CELL TECHNOLOGIES). The obtained clones were examined in further detail using Biacore (GE Healthcare), and CP11-1 was selected.

Monoclonal antibody CP11-1 is produced by a hybridoma that has been deposited as the accession number "NITE BP-02021" with the Patent Microorganisms Depositary (NPMD) of the National Institute of Technology and Evaluation.

(2) Method for Producing Monoclonal Antibodies HMa166 and HMa186

100 μg of rhHMGB1 antigen together with Freund's complete adjuvant (FCA) were used for the initial immunization of mice (Balb/c). Fourteen days later, as a booster, 50 μg of the rhHMGB1 antigen was used with Freund's incomplete adjuvant (FIA) for immunization. Thereafter, with 14-day intervals, immunization was carried out four times in total using 50 μg of rhHMGB1 antigen with FIA. After the final immunization, the spleen was removed, and lymphocytes were prepared according to a standard method, and they were fused with myeloma Sp2/0-Ag14 (ATCC: CRL-1581). The fused hybridomas were cultured and cloned by a limiting dilution method according to a standard method, and this was subjected to screening by ELISA, and 18 clones were obtained. A total of 19 clones including the obtained 18 clones and CP11-1 were individually immobilized onto the sensor chip of Biacore (GE Healthcare) via an anti-mouse IgG antibody, and after binding of rHMGB1, the respective antibodies were added, and the affinity to rHMGB1 was examined in detail, and combinations of antibodies against different epitopes were selected. As a result, HMa166 and HMa186, regardless of which is immobilized, showed strong reaction with rHMGB1, and do not interfere with each other when each of them binds to HMGB1. Thus, it was considered that HMa166 and HMa186 recognize different epitopes (Table 1).

TABLE 1

Epitope Mapping of HMGB1 Monoclonal Antibodies

| Primary Antibody | Secondary Antibody | | | | | | | | | | | | | | | | | | |
|---|---|---|---|---|---|---|---|---|---|---|---|---|---|---|---|---|---|---|---|
| | 1-2 | 2 | 11-2 | 33 | 34-2 | 74 | 87 | 91 | 94 | 115 | 135 | 145 | 166 | 168 | 176 | 186 | 231 | 235 | GP11-1 |
| 1-2 | | + | − | − | − | + | + | + | + | − | + | − | + | + | + | + | − | + | + |
| 2 | − | | − | − | − | − | − | + | − | − | + | − | − | − | − | − | − | − | + |
| 11-2 | − | − | | − | − | + | + | + | − | − | + | − | + | + | + | + | − | − | + |
| 33 | + | + | + | | + | + | + | − | + | − | + | − | + | + | + | + | − | + | − |
| 34-2 | − | + | − | − | | − | + | + | + | − | + | − | + | + | + | + | − | + | + |
| 74 | − | − | + | − | − | | − | + | − | − | +++ | − | − | − | +++ | +++ | − | − | + |
| 87 | + | − | + | − | + | − | | + | − | − | + | − | − | − | +++ | +++ | − | − | − |
| 91 | + | + | + | − | + | +++ | + | | + | − | − | − | + | + | − | − | − | + | − |
| 94 | + | − | − | − | + | − | − | + | | − | + | − | − | − | + | + | − | − | + |
| 115 | + | + | + | − | + | + | − | + | + | | + | − | + | + | + | + | − | + | − |
| 135 | + | + | + | − | + | +++ | + | − | + | + | | − | + | + | + | + | − | + | + |
| 145 | + | − | + | − | + | + | − | − | − | − | − | | − | − | + | + | − | − | − |
| 166 | + | − | + | − | + | − | − | + | − | − | + | − | | − | +++ | +++ | − | − | + |
| 168 | + | − | + | − | + | − | − | + | − | − | + | − | − | | +++ | +++ | − | − | + |
| 176 | + | + | + | + | + | +++ | +++ | − | +++ | +++ | − | + | +++ | +++ | | − | + | +++ | +++ |
| 186 | + | +++ | + | − | + | +++ | +++ | + | + | +++ | + | − | +++ | +++ | + | | + | +++ | +++ |
| 231 | + | + | + | − | + | +++ | + | + | + | − | + | − | + | + | + | + | | + | + |
| 235 | + | − | − | − | + | + | − | +++ | − | − | +++ | − | + | + | +++ | +++ | − | | + |
| CP11-1 | +++ | +++ | +++ | − | +++ | +++ | +++ | +++ | +++ | − | +++ | − | +++ | +++ | +++ | +++ | + | +++ | |

+++ Clear binding of secondary antibody (different epitopes)/Same reactivity even when the primary and secondary antibodies are interchanged. The optimum pair is selected from these antibody pairs.
+++ Clear binding of secondary antibody (different epitopes)/Different reactivity when the primary and secondary antibodies are interchanged.
+ Weaker binding of secondary antibody (the recognition sites overlap or are regions nearby).
− No observed binding of secondary antibody (same epitope).

Monoclonal antibodies HMa166 and HMa186 are produced by hybridomas deposited as accession numbers "NITE BP-02020" and "NITE-BP-02019", respectively, with the Patent Microorganisms Depositary (NPMD) of the National Institute of Technology and Evaluation.

(3) Screening Method for Monoclonal Antibody Production

For screening, the culture supernatant of each clone was added to an ELISA plate prepared by immobilizing 50 µL of rhHMHB1 (2 µg/mL) by a standard method and then blocking it using ImmunoBlock (DS Pharma Biomedical) diluted five-fold with purified water, and this was incubated for two hours and then washed. Subsequently, HRP-labeled anti-mouse IgG was added thereto as a secondary antibody, and this was incubated for two hours and then washed. Coloring substrate TMBZ (KPL) was added according to a standard method, and the reaction was stopped using phosphoric acid, and the absorbance at 450 nm was measured using a microplate reader.

3. Epitope Analysis of Monoclonal Antibodies HMa166 and HMa186

Epitopes of monoclonal antibodies HMa166 and HMa186 were examined by analyzing the binding of various peptides of HMGB1 with the antibodies using Biacore. As a control, a similar examination was performed using monoclonal antibody CP11-1 obtained by immunization with Peptide No. 5 (KPDAAKKGVVKAEK/SEQ ID NO: 6).

As a result, Peptide No. 1 ($G_2$-$A_{17}$) (GKGDPKKPRGKMSSYA/SEQ ID NO: 1) bound to HMa166, and the stability of the antigen/antibody complex which indicates the amount of binding after washing was also observed. Peptide No. 3 ($K_{65}$-$Y_{78}$) (KADKARYEREMKTY/SEQ ID NO: 3) also bound to HMa166; however, since the stability of the complex was low, it was thought that this would be non-specific absorption (FIG. 2A).

Furthermore, HMa186 did not show affinity to any of Peptide Nos. 1.2, 3, 4, and 5 (FIG. 2B).

CP11-1 showed affinity and stability of the antigen/antibody complex only with Peptide No. 5 (KPDAAKKGVVKAEK/SEQ ID NO: 6) used for immunization (FIG. 2C).

Furthermore, monoclonal antibodies HMa166 and HMa186 were examined by analyzing their affinity to HMGB1-NT using Biacore. Recombinant human HMGB1 was used as a control.

As a result, HMGB1-NT ($M_1$-$K_{82}$) (MGKGDPKKPRGKMSSYAFFVQTCREEHKKKHP-DASVNFSEFSKKCSERWKTMSAKE KGKFED-MAKADKARYEREMKTYIPPK/SEQ ID NO: 4) showed affinity to both monoclonal antibodies HMa166 and HMa186 (FIG. 3A, B).

Furthermore, the reactivity of HMGB1-NT ($M_1$-$K_{82}$) (MGKGDPKKPRGKMSSYAFFVQTCREEHKKKHP-DASVNFSEFSKKCSERWKTMSAKE KGKFED-MAKADKARYEREMKTYIPPK/SEQ ID NO: 4) and recombinant human HMGB1 to each of the monoclonal antibodies was confirmed by dot blotting.

100 ng of each protein was spotted onto a PVDF membrane, and 20% ImmunoBlock (DS Pharma) was used for blocking at room temperature for two hours, and this was washed with TBSt. Then, each antibody was added at 1 µg/mL to 10% ImmunoBlock-containing PBS, and incubation was performed at room temperature for two hours. After washing, HRP-labeled anti-mouse IgG (GE Healthcare #NA931 V) diluted 10000-fold in 10% ImmunoBlock-containing PBS was reacted at room temperature for one hour. After washing, color development was performed using ECL Prime Western Blotting Detection Reagent (GE Healthcare #RPM2236).

Figure 4:
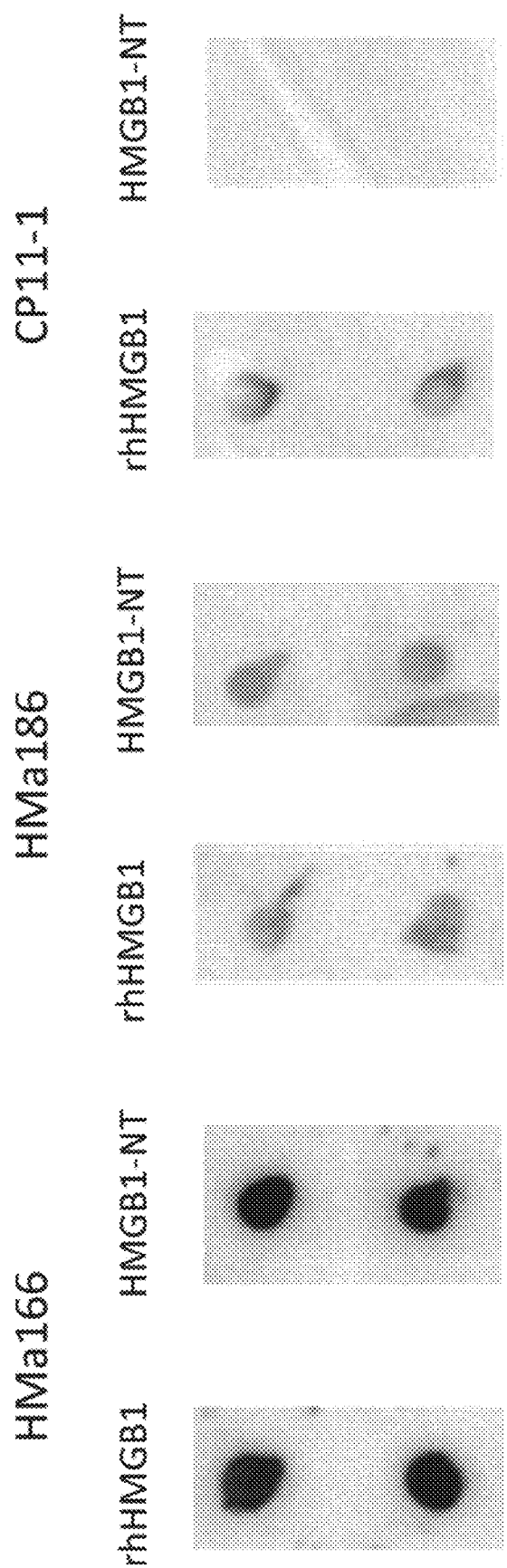
FIG. 4 presents photographs indicating the reactivity of each antibody by dot blotting.

As a result, monoclonal antibodies HMa166 and HMa186 showed affinity to HMGB1-NT and recombinant human HMGB1. CP11-1 showed affinity only to recombinant human HMGB1 (FIG. 4).

Figure 5:
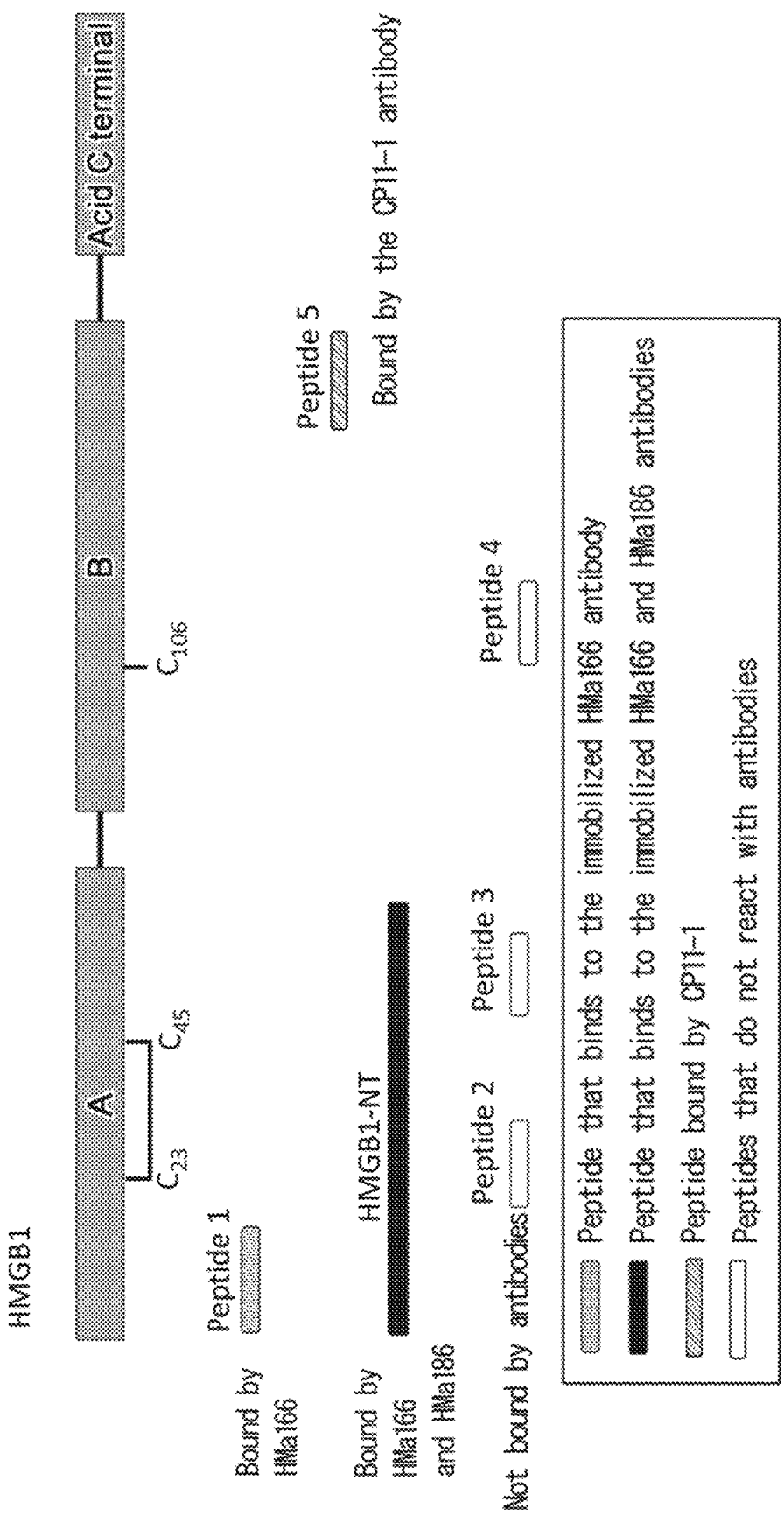
FIG. 5 shows a schematic diagram of the reactivity of each antibody to the human HMGB1 peptides.
Figure 6:
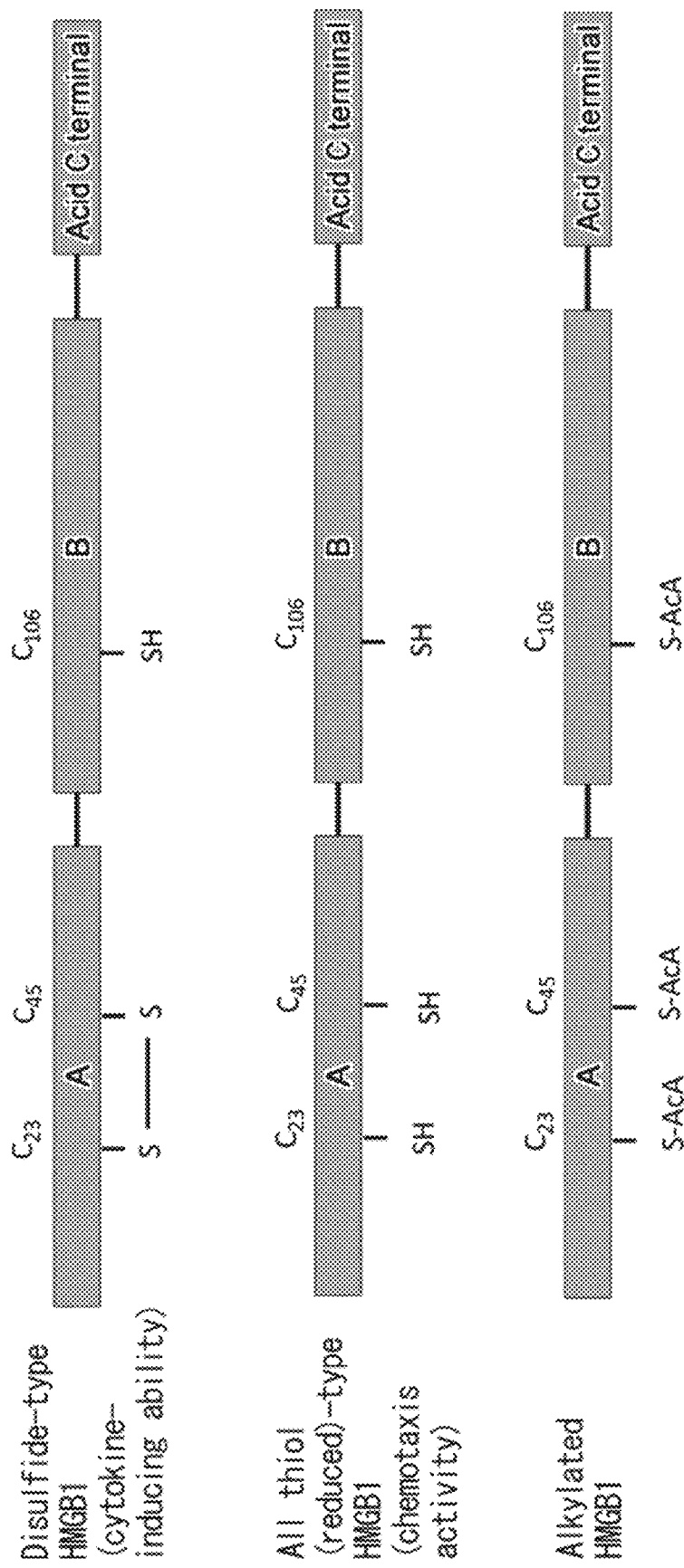
FIG. 6 shows a schematic diagram of the redox states of HMGB1.

HMa166 and HMa186 were thought to recognize different epitopes (Table 1), and they did not react with Peptide No. 2 ($C_{23}$-$F_{38}$) (CREEHKKKHPDASVNF/SEQ ID NO: 2) or Peptide No. 3 ($K_{65}$-$Y_{75}$) (KADKARYEREMKTY/SEQ ID NO: 3). Therefore, the possibility that HMa186 recognizes the structure near cysteine at position 45 ($C_{45}$) or the three-dimensional structure where the disulfide bond is formed by cysteines at position 23 ($C_{23}$) and position 45 ($C_{45}$) was considered (FIG. 5).

4. Confirmation of the Redox State of *E. coli* Recombinant Human HMGB1.

The redox state of purified recombinant human HMGB1 was confirmed by the following method.

There are reports showing that, in disulfide-type HMGB1 having cytokine-inducing ability, cysteines at position 23 ($C_{23}$) and position 45 ($C_{45}$) form a disulfide bond; whereas, in reduced-type HMGB1 which is involved in chemotaxis but does not have cytokine-inducing ability, this disulfide bond has been reduced. To conveniently determine which of the redox states a purified recombinant human HMGB1 is in, SDS-PAGE was performed, and their molecular weights were compared.

To prevent oxidation (disulfide bond formation) of the purified recombinant human HMGB1, 10 mM glutathione and 1 mM EDTA were added, then 2× sample buffer (Daiichi Kagaku Yakuhin) (0.125 M Tris-HCl [pH 6.8], 4.3% SDS, 30% Glycerol, 0.01% BPB) was added in the presence or absence of 10% β-ME. After incubation at room temperature for ten minutes, SDS-PAGE was performed using 4-15% acrylamide gradient gel (Bio-Rad). As a control, SDS-PAGE was performed in the same manner using conunercially available disulfide HMGB1 (HMGBiotech).

Figure 7:
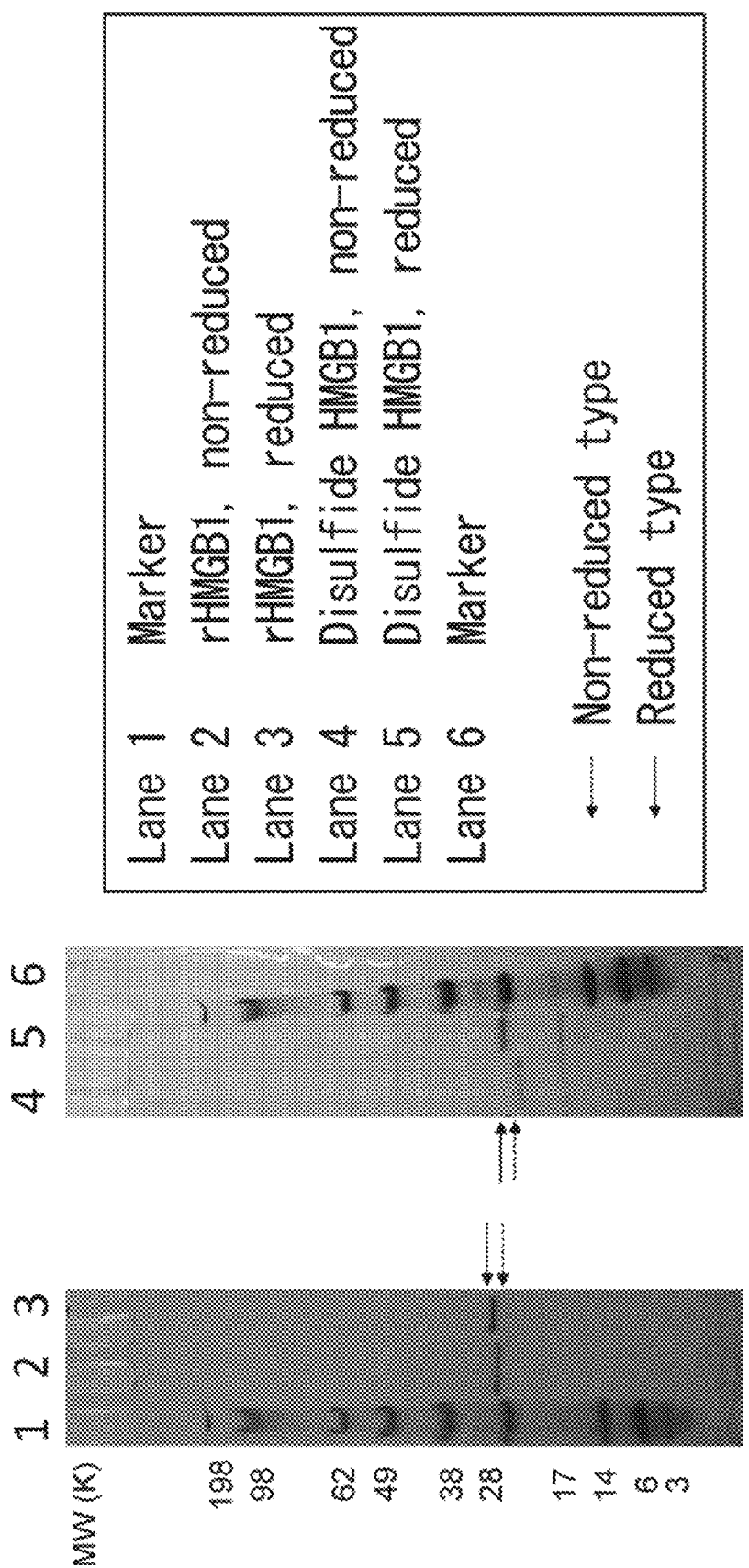
FIG. 7 presents photographs showing SDS-PAGE of recombinant human HMGB1.

As a result, since commercially available disulfide HMGB subjected to SDS-PAGE under non-reducing conditions in the absence of β-ME retained the disulfide bond, the molecule was folded and the calculated molecular weight in SDS-PAGE was as low as 23.3 kDa (FIG. 7, Lane 4). On the other hand, since in commercially available disulfide HMGB subjected to SDS-PAGE under reducing conditions in the presence of β-ME, the disulfide bond was cleaved, and the folded structure of the molecule became cancelled, and thus the calculated molecular weight in SDS-PAGE was increased to 24.9 kDa (FIG. 7, Lane 5).

The indicated molecular weights for recombinant human HMGB1 are higher than those of the commercially available HMGB1 because the recombinant human HMGB1 has an expression vector-derived sequence added to its N terminus. Its value under non-reducing condition was as low as 26.7 kDa (FIG. 7, Lane 2), and its value under reducing condition was as high as 27.4 kDa (FIG. 7, Lane 3). Accordingly, recombinant human HMGB1 was thought to retain its disulfide bond as with disulfide-type HMGB1.

5. Preparation of Reduced-Type Human Recombinant HMGB1

Reduced-type HMGB1 was prepared by the following method. To purified recombinant human HMGB1 (1 mg/mL), DTT was added at 20 mM, and this was incubated at 37° C. for 60 minutes. Thereafter, buffer exchange was performed using a Nap-5 column for buffer exchange (GE Healthcare) equilibrated using PBS containing 20 mM glutathione.

6. Preparation of Alkylated Human Recombinant HMGB1

As with reduced-type human recombinant HMGB1, DTT was added at 20 mM to alkylated HMGB1, and this was incubated at 37° C. for 60 minutes. After reduction, iodoacetamide (GE Healthcare) was added at 40 mM, and this was incubated at room temperature for 30 minutes. Thereafter, to inactivate excessive iodoacetamide, DTT was added at 10 mM. Then, buffer exchange was performed using a Nap-5 column for buffer exchange (GE Healthcare) equilibrated using PBS containing 20 mM glutathione.

Disulfide-type HMGB1 was subjected to buffer exchange using a Nap-5 column for buffer exchange (GE Healthcare) equilibrated with PBS containing 20 mM glutathione.

Protein quantification was performed by the Bradford staining method (Bio-Rad).

7. Disulfide Human Recombinant HMGB1-Specific Antibodies

For the three types of anti-HMGB1 monoclonal antibodies, i.e., HMa116, HMa186, and CP11-1, the reactivity to disulfide-type human recombinant HMGB1, reduced-type human HMGB1, and alkylated human recombinant HMGB1 was examined using an intermolecular interaction-measuring apparatus, Biacore (GE Healthcare).

An anti-mouse IgG antibody was immobilized onto a sensor chip by covalent bond, and after blocking with mouse IgG (Rockland Inc.), each of the monoclonal antibodies at 20 μg/mL was individually bound. After washing, 20 μg/mL of disulfide-type human recombinant HMGB1, reduced-type recombinant human HMGB1, and alkylated human recombinant HMGB1 were bound, and the amount of binding was measured.

Figure 8:
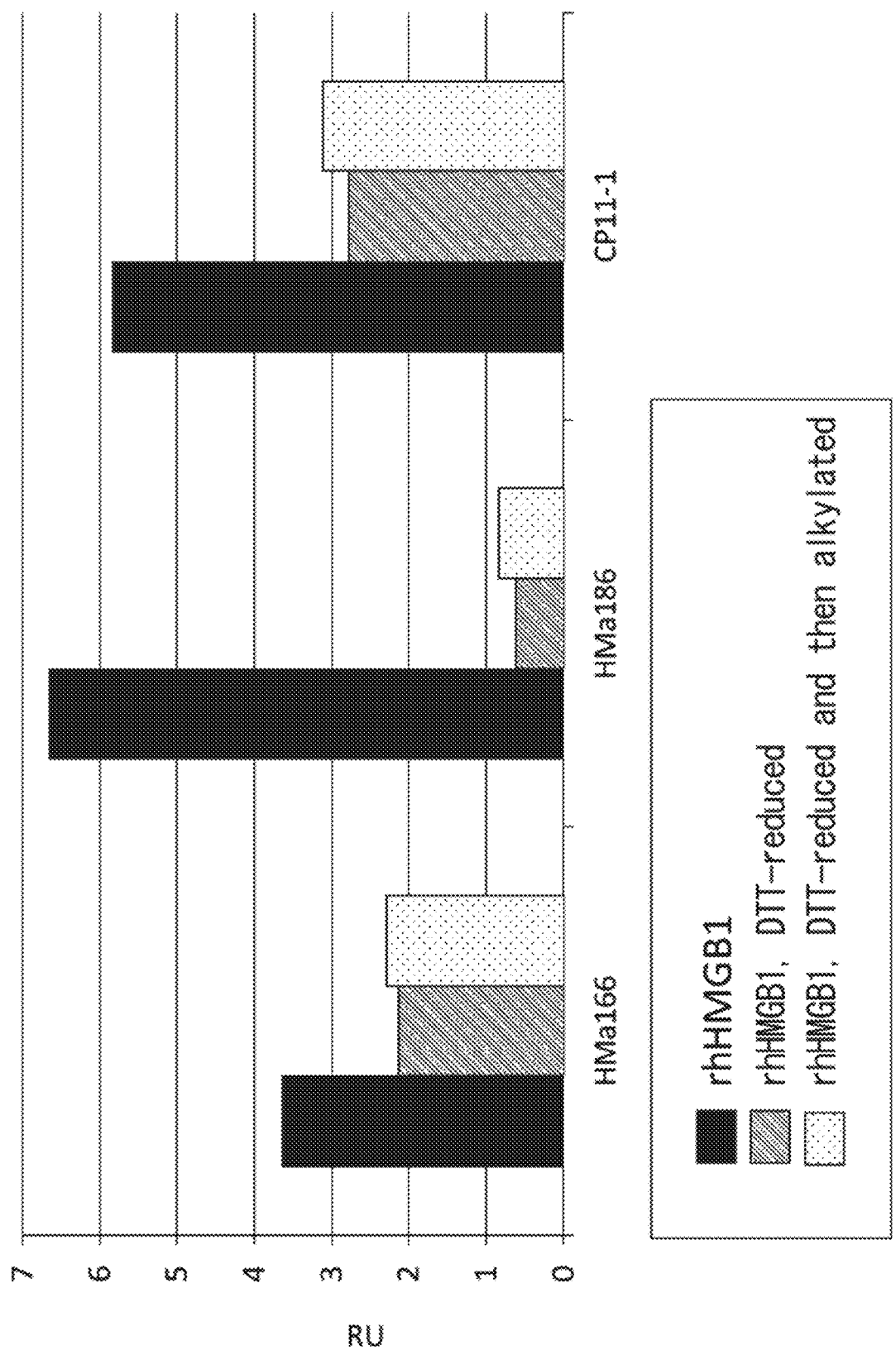
FIG. 8 presents a graph showing the reactivity between each antibody and disulfide-type/reduced/alkylated rhHMGB1.

As a result, HMGB1 of three types of structures, i.e., disulfide-type human recombinant HMGB1, reduced-type human recombinant HMGB1, and alkylated human recombinant HMGB1, bound to monoclonal antibodies HMa166 and CP11-1. On the other hand, only disulfide-type human recombinant HMGB1 bound to HMa186, but not to reduced-type human recombinant HMGB1 or alkylated human recombinant HMGB1 (FIG. 8). That is, the HMa186 monoclonal antibody was found to be an antibody that specifically recognizes the disulfide bond region formed by cysteine $C_{23}$ at position 23 and cysteine $C_{45}$ at position 45 of disulfide-type HMGB1 which has cytokine-inducing ability.

8. Preparation of Thrombin-Cleaved HMGB1

WO2014/147873 A1 reports that HMGB1 is cleaved by thrombin between arginine at position 10 ($R_{10}$) and glycine at position 1 ($G_{11}$) (N-terminal M1-R10 of HMGB1 is cleaved off), and des-HMGB1 which is a HMGB1 degradation product and has "GKMSS . . . " (SEQ ID NO: 76) as the newly exposed N-terminal amino acid residues. Furthermore, WO2014/147873 A1 reports that des-HMGB1 is inactivated and has lowered cytotoxicity (WO2014/147873 A1, page 3, lines 15-22)

Figure 9:
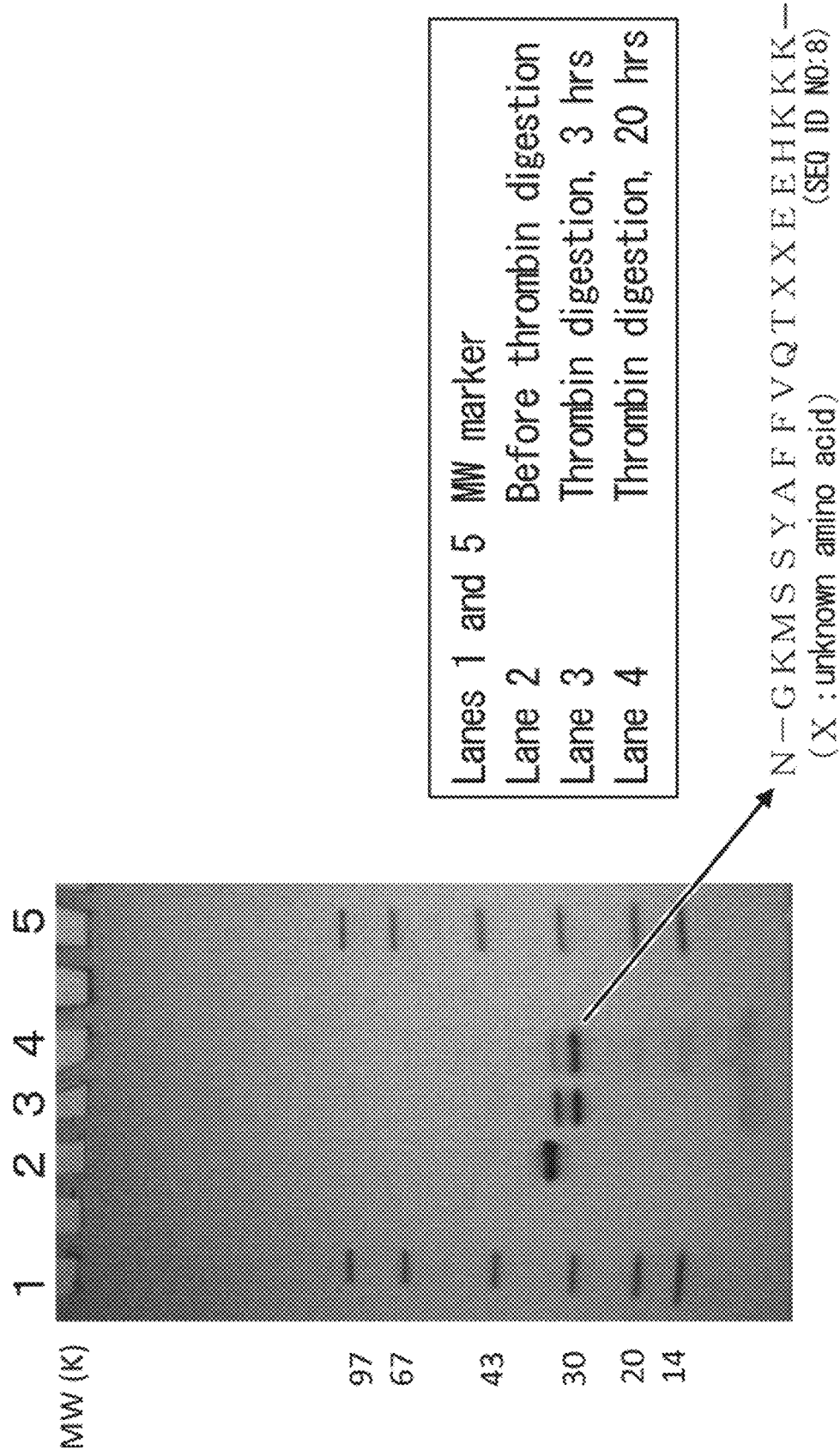
FIG. 9 presents a photograph showing SDS-PAGE of thrombin-digested HMGB1 and the analysis of the N-terminal amino acid sequence (SEQ ID NO: 8).

Accordingly, the reactivity of each of the monoclonal antibodies to thrombin-cleaved HMGB1 was investigated. Thrombin cleavage was performed using a Thrombin Clean Cleave kit manufactured by Sigma-Aldrich according to the manufacturer's instructions. To 90 μL of human recombinant HMGB1 at 1 mg/mL, 10 μL of 10× buffer was added, and then washed thrombin-agarose was added, and this was incubated at 37° C. for three hours or 20 hours. After incubation, this was centrifuged at 500×g to remove thrombin-agarose, and SDS-PAGE was performed, and decrease in molecular weight was confirmed (FIG. 9). Furthermore, after SDS-PAGE, electrotransfer to a PVDF membrane was performed by a standard method using a transblotter (Bio-Rad), and a band suspected to be thrombin-cleaved HMGB1 was cut out, and N-terminal amino acid sequence analysis was performed using a protein sequencer (ABI). As a result, the determined sequence was N-GKMSSYAFFVQTXXEEHKKK-C (X: unknown amino acid/SEQ ID NO: 8), and this was verified to be equivalent to the sequence of des-HMGB1 (FIG. 9).

9. Reactivity of the Antibodies to des-HMGB1

The affinity between des-HMGB1 and anti-HMGB1 monoclonal antibody HMa166 or Hma186 was examined using Biacore (GE Healthcare).

An anti-mouse IgG antibody was immobilized onto a sensor chip by covalent bond, and after blocking with mouse IgG (Rockland Inc.), each of the monoclonal antibodies at 20 μg/mL was individually bound. After washing, 20 μg/mL of des-HMGB1 was bound, and the amount of binding was measured.

Figure 10:
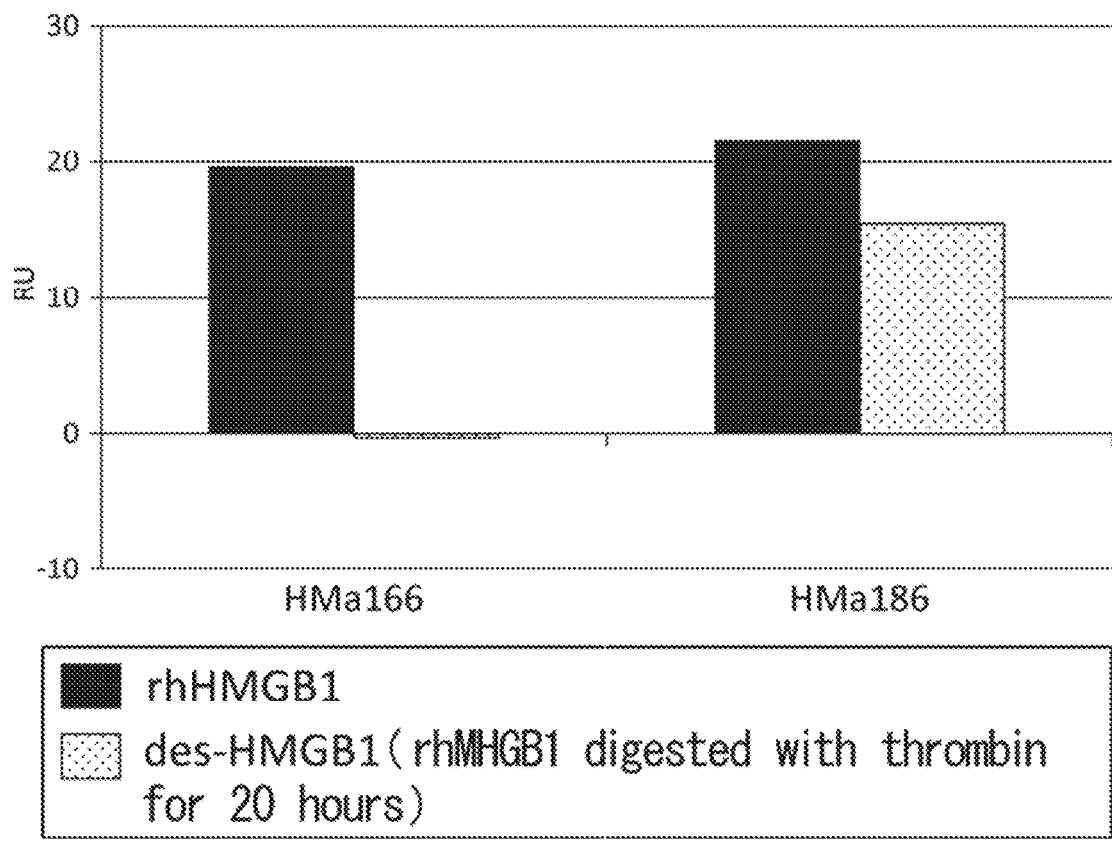
FIG. 10 presents a graph showing the reactivities of the HMa166 and HMa186 antibodies to thrombin-digested rhHMGB1 (des-HMGB1).

As a result, HMa166 no longer reacted with des-HMGB1, but HMa186 was also able to bind to des-HMGB1 (FIG. 10).

10. Preparation of ELISA which can Measure Disulfide-Type HMGB1

100 μL of anti-HMGB1 antibody HMa186 at 10 μg/mL was added to a 96-well ELISA plate (Maxsorp, Nunc), and the antibody was immobilized by a standard method, and then 200 μL of ImmunoBlock (DS Pharma Biomedical) diluted five-fold with purified water was dispensed to perform blocking. After washing with TBSt (10 mM Tris pH7.4, 150 mM NaCl, 0.05% Tween-20), recombinant HMGB1 was added at 0 ng/mL to 80 ng/mL, and this was reacted at room temperature for two hours, then washed with TBSt. Then, HRP-labeled anti-HMGB1 antibody CP11-1 was added, and this was washed, and then coloring substrate TMBZ (KPL) was added according to a standard method, and the reaction was stopped using phosphoric acid. The absorbance at 450 nm was measured using a microplate reader.

Figure 11:
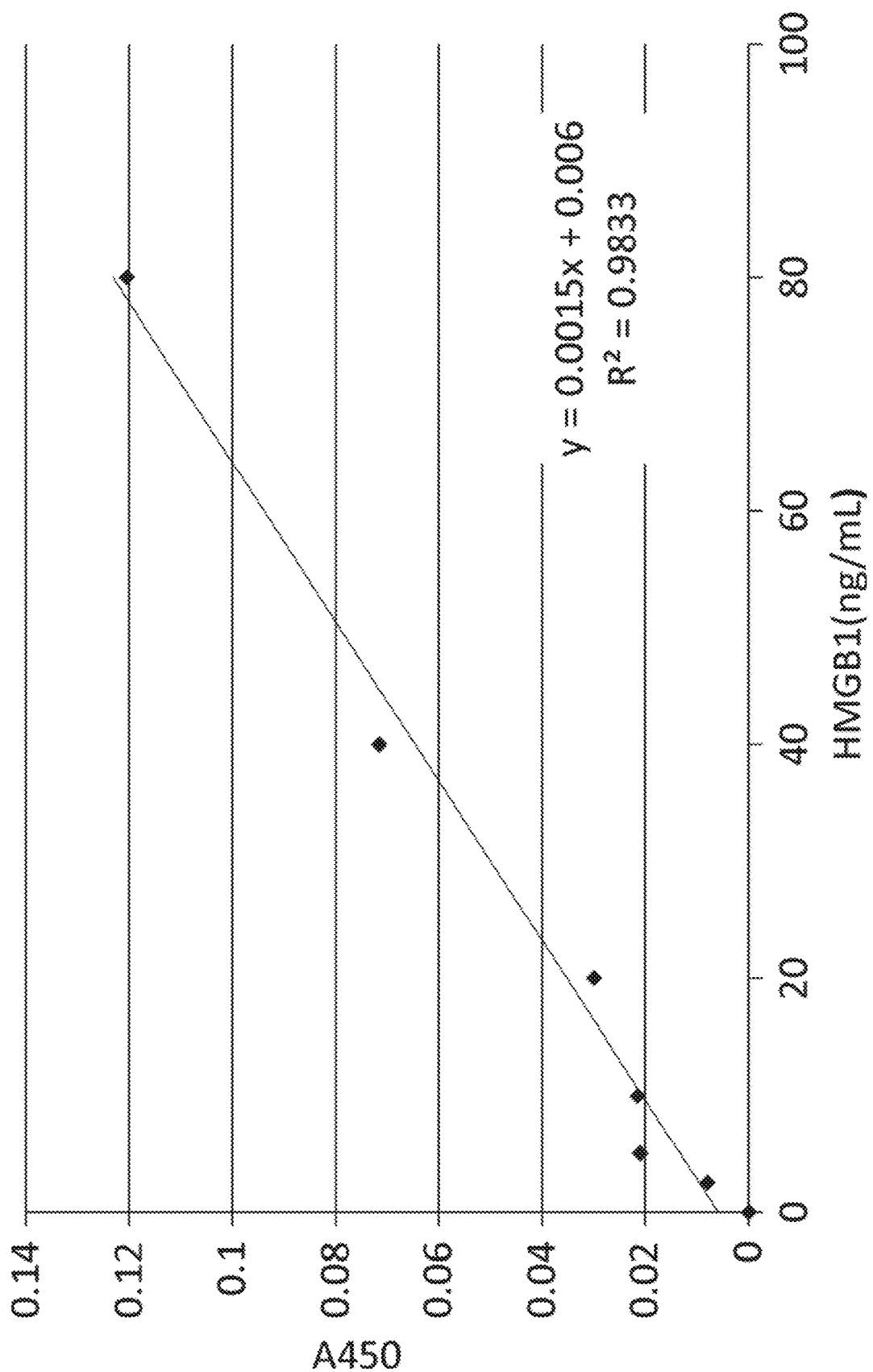
FIG. 11 presents a graph showing results of disulfide-type-specific HMGB1 ELISA measured by immobilization of HMa186.

As a result, linearity was obtained with recombinant HMGB1 at 2.5 ng/mL to 80 ng/mL (FIG. 11).

11. Preparation of ELISA that can Measure Total HMGB1

To accurately grasp the progression, course, and such of a pathological condition, it is important to measure not only disulfide-type HMGB1 having cytokine-inducing ability, but also reduced-type HMGB1 and cleaved des-HMGB1. Therefore, by using HMa166 and HMa186 in combination, ELISA that can measure all of HMGB1 (total HMGB1) including disulfide-type HMGB1, reduced-type HMGB1, and des-HMGB1, was prepared.

100 μL of HMa166 and HMa186 mixed to be 10 μg/mL was added to a 96-well ELISA plate (Maxsorp. Nunc), and the antibodies were immobilized by a standard method, and then 200 μL of ImmunoBlock (DS Pharma Biomedical) diluted five-fold with purified water was dispensed to perform blocking. After washing with TBSt (50 mM Tris pH7.4, 150 mM NaCl, 0.05% Tween-20), recombinant HMGB1 was added at 0 ng/mL to 80 ng/mL, and this was reacted at room temperature for two hours. After washing with TBSt, the HRP-labeled anti-HMGB1 antibody CP11-1 was added, and this was washed. Then, coloring substrate TMBZ (KPL) was added according to a standard method, and the reaction was stopped using phosphoric acid, and the absorbance at 450 nm was measured using a microplate reader.

Figure 12:
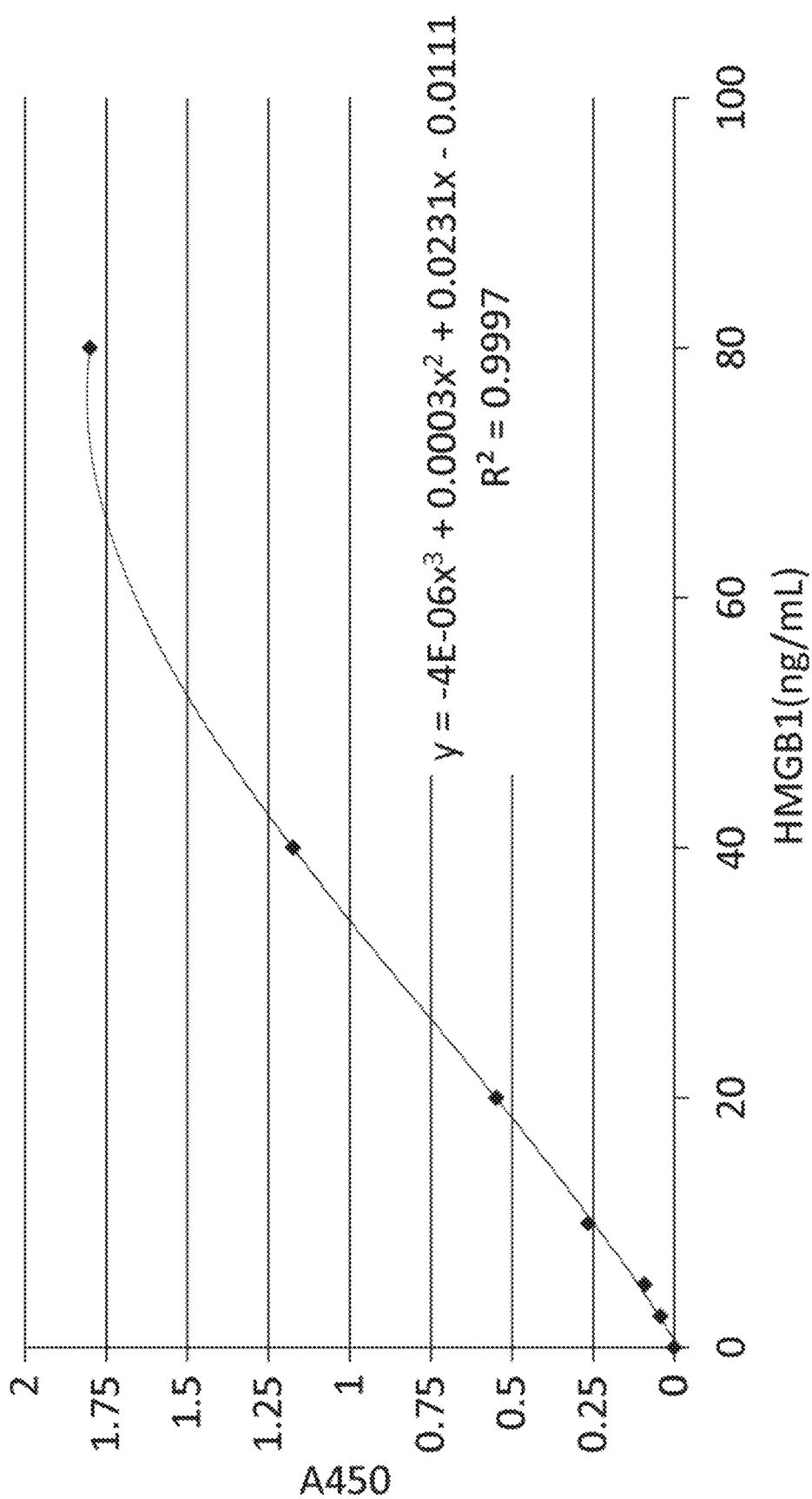
FIG. 12 presents a graph showing results of total HMGB1 ELISA measured by immobilization of both of the HMa186 and HMa166 antibodies.

As a result, linearity was obtained with recombinant HMGB1 at 2.5 ng/mL to 80 ng/mL (FIG. 12).

12. Optimization of ELISA for Measuring Total HMGB1

In antigen/antibody reactions such as ELISA, some antibodies are interfered even in a salt concentration or pH range used in common antigen/antibody reactions, and sometimes they cannot react efficiently. Accordingly, optimum salt concentration and pH for the reaction buffer used in ELISA for measuring total HMGB1 were examined by addition/recovery experiments. 100 µL of HMa166 and HMa186 mixed to be 10 µg/mL was added to a 96-well ELISA plate (Maxsorp, Nunc), and the antibodies were immobilized by a standard method, and then 300 µL of 100 mM Tris-HCl (pH8.8) with 1% BSA was dispensed to perform blocking. This was washed with TBSt (50 mM Tris-HCl (pH7.4), 150 mM NaCl, 0.05% Tween-20). Human pooled plasma (Kohjin Bio) was diluted ten-fold with the following buffers where pH was adjusted to 7.0, 7.5, 8.0, 8.5, and 9.0:

5% BSA, 100 mM Tris-HCl containing 0.1% Tween-20, 100 mM NaCl buffer (total salt concentration: 200 mM);

5% BSA, 100 mM Tris-HCl containing 0.1% Tween-20, 40 mM NaCl buffer (total salt concentration: 140 mM);

5% BSA, 20 mM Tris-HCl containing 0.1% Tween-20, 100 mM NaCl buffer (total salt concentration: 120 mM).

Additionally, 20 ng of recombinant HMGB1 was added, and this was allowed to react at 37° C. for two hours. After washing with TBSt, the HRP-labeled anti-HMGB1 antibody CP11-1 which was diluted to 2 µg/mL using HRP Protector (CANDOR Bioscience GmbH) was added, and this was reacted at room temperature for one hour. After washing, coloring substrate TMBZ (KPL) was added according to a standard method, and the reaction was stopped using phosphoric acid, and the absorbance at 450 nm was measured using a microplate reader. The recovery rate was calculated by subtracting the HMGB1 concentration in the pooled plasma measured for each condition from the actually measured HMGB1 value, and dividing the obtained value by the amount of addition, 20.

Figure 13:
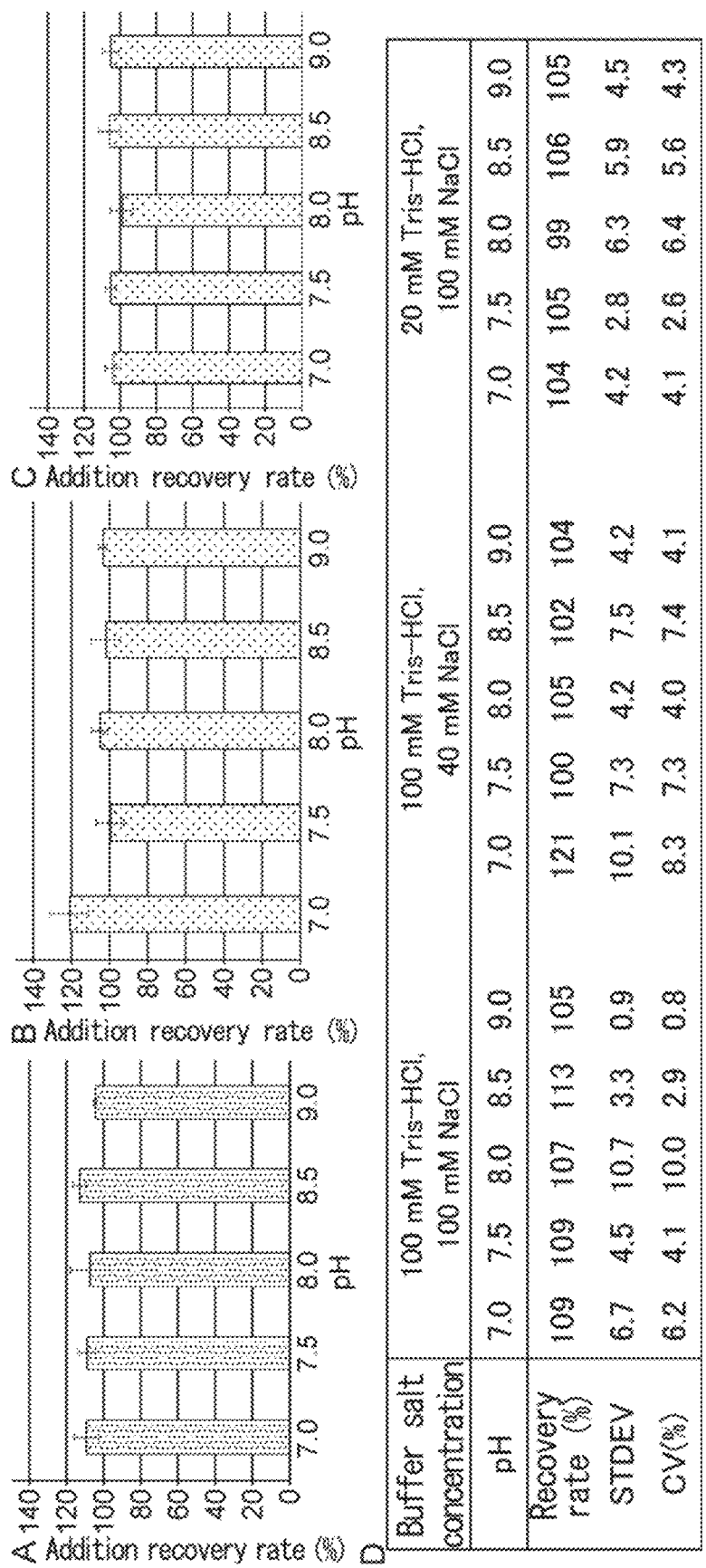
FIG. 13 shows results of optimization studies on total HMGB1 ELISA measurements.

As a result, when the addition recovery rates of HMGB1 added to and recovered from human pooled plasma were compared, no large differences were observed, and the recovery rates were nearly within 100%±10% when the buffers were used at any of the salt concentrations except that a recovery rate of 121% was obtained when 100 mM Tris-HCl (pH7.0) with 40 mM NaCl was used as the buffer. It was found that ELISA in this case was not affected by differences in buffer salt concentrations at around 150 mM which are physiological salt concentrations often used in ELISA and such. Furthermore, also for pH, no large influences were found for pH values from 7.0 to 9.0 often used in ELISA and such (FIG. 13).

13. Sequences of the CDR Regions of HMa166 and HMa186

(1) RNA Extraction 0.75 mL of Trizol LS Reagent (Invitrogen, Inc.) was added to HMa166- and HMa186-producing hybridomas (1×10$^7$ cells), and the cells were directly dissolved by pipetting up and down. After incubating at room temperature for five minutes, 0.2 mL of chloroform was added, and this was mixed by shaking vigorously for 15 seconds. After incubation at room temperature for 15 minutes, this was subjected to centrifugation at 12,000 g for 15 minutes at 4° C. After centrifugation, the aqueous layer was collected, and 0.5 mL of isopropanol was added, and this was incubated at room temperature for ten minutes, and then subjected to centrifugation at 12,000 g for ten minutes at 4° C. 1 mL of 80% ethanol was added to the obtained precipitate, and the precipitate was washed, dried, and then dissolved in RNAse-free water to yield the RNA.

(2) cDNA Synthesis cDNA synthesis was performed using PrimeScript II 1st strand cDNA Synthesis Kit (TAKARA BIO Inc.). 5 µM oligo dT primer, 1 mM dNTP, and RNase-free water were added to 2 µg of the RNA, to make the volume 10 µL, and this was incubated at 65° C. for five minutes. Thereafter, 5× PrimeScript II Buffer, RNase Inhibitor 20 U, PrimeScript IIRTase 200 U, and RNase-free water were added to make the volume 20 µL. After incubating the mixed solution at 42° C. for 45 minutes, this was heated to 72° C. for 15 minutes.

(3) PCR of the CDR Regions

The CDR regions were cloned according to the method of Wang et al. (J. Immunol. Method 2000, 233, 167-177). TaKaRa Ex Taq (TAKARA BIO Inc.) was used for the PCR enzyme. For PCR for the heavy chain, IgG1 primer (5'-ATAGACAGATGGGGGTGTCGTTTGGC-3'/SEQ ID NO: 64) and 5' MH1 primer (5'-SARGTNMAGCTGSAGSAGTC-3'/SEQ ID NO: 65) were used as a set; and for PCR for the light chain, 3' KC primer (5'-GGATACAGTTGGTGCAGCATC-3'/SEQ ID NO: 66) and 5' MK primer (5'-GAYATTGTGMTSACMCARWCTMCA-3'/SEQ ID NO: 67) were used as a set.

1 µL of cDNA, 4 µL of 10× ExTaq buffer, 3.2 µL of dNTP, 0.5 µM each of the primer set, 1 U ExTaq, and sterilized purified water were added to make the volume 40 µL. The mixed solution was subjected to denaturation at 94° C. for three minutes; then repetition of 30 cycles of 94° C. for 30 seconds, 48° C. for 30 seconds, and 72° C. for 30 seconds; and then elongation reaction at 72° C. for three minutes.

(4) Cloning of the CDR Regions

Each of the obtained heavy-chain and light-chain PCR products was purified, and TA-cloned into the pT7 T-vector (Novagen). After incubation at 16° C. for one day and night, the ligated product was used to transform *E. coli* JM109, the cells were inoculated into LB agar medium containing 50 µg/mL ampicillin, and this was cultured overnight. The grown colonies were picked, and template DNAs prepared by the boiling method were subjected to PCR.

(5) Sequences of the CDR Regions

TaKaRa Ex Taq (TAKARA BIO Inc.) was used for the PCR enzyme. 1 µL of template DNA, 4 µL of 10× ExTaq buffer, 3.2 µL of dNTP, 0.5 µM each of the M13U primer (5'-TGTAAAACGACGGCCAGT-3'/SEQ ID NO: 68) and M13R primer (5'-GAAACAGCTATGACCATG-3'/SEQ ID NO: 69), 1 U ExTaq, and sterilized purified water were added to make the volume 40 µL. The mixed solution was subjected to denaturation at 94° C. for three minutes; then repetition of 30 cycles of 94° C. for 30 seconds, 55° C. for 30 seconds, and 72° C. for 30 seconds; and then elongation reaction at 72° C. for three minutes. The obtained PCR products were purified, and sequencing reaction was performed by a standard method using each of the M13U and M13R primers, and sequencing was performed using an ABI 3100 Genetic Analyzer (Applied Biosystems)

(6) Sequence Analysis of the CDR Regions

Figure 16:
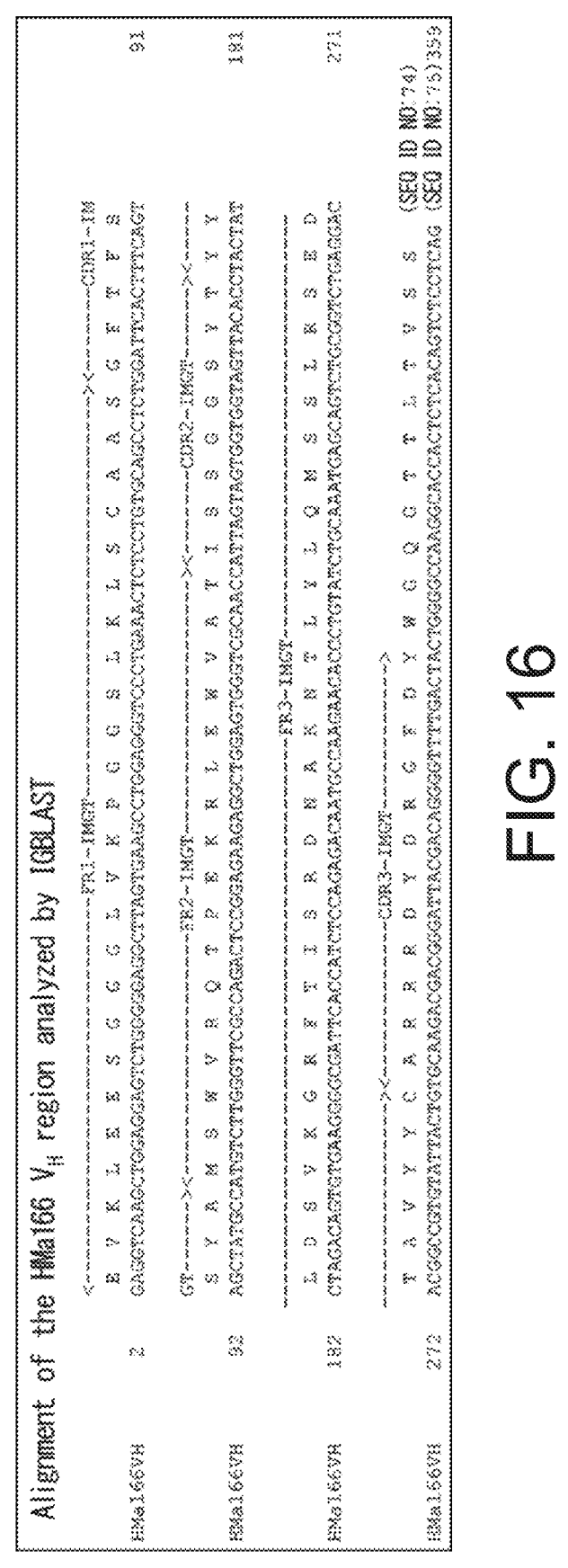

The obtained sequences were verified using the sequencer, and the CDR regions were analyzed using IGBLAST (www.ncbi.nlm.nih.gov/igblast/). The results are shown in FIGS. 14 to 16.

The invention claimed is:

1. An antibody which comprises a heavy chain variable region comprising the amino acid sequence of SEQ ID NO: 47, and a light chain variable region comprising the amino acid sequence of SEQ ID NO: 49.

2. A monoclonal antibody HMa186 produced by a hybridoma identified by accession number MTh BP-02019.

3. A low-molecular-weight antibody of the antibody of claim 1 or 2.

4. A fragment of the antibody of claim 1 or 2, which has specific binding activity to disulfide-type high mobility group box 1 (HMGB1).

5. A chimeric antibody or humanized antibody of the antibody of claim 1 or 2.

6. A human antibody of the antibody of claim 1 or 2.

7. A method for producing a chimeric antibody or humanized antibody of the antibody of claim 1 or 2, which comprises linking a DNA encoding a variable region of the antibody of claim 1 or 2 with a DNA encoding a constant region of the antibody of claim 1 or 2 to form a linked constant and variable region; inserting the linked constant and variable region into an expression vector; introducing the vector into a host; and producing the variable region and the constant region of the antibody.

8. A kit or reagent for measuring or detecting total high mobility group box 1 (HMGB1) in a sample, which comprises the antibodies of (a) and (b) below:
   (a) the antibody of claim 1 or 2; and
   (b) a monoclonal antibody HMa166 produced by a hybridoma identified by accession number MTh BP-02020.

9. The kit or reagent of claim 8, wherein total high mobility group box 1 (HMGB1) includes disulfide-type HMGB1, reduced-type HMGB1, and thrombin-cleaved HMGB1.

10. A monoclonal antibody HMa166 produced by a hybridoma identified by accession number NITE BP-02020.

11. A monoclonal antibody CP11-1 produced by a hybridoma identified by accession number NITE BP-02021.

* * * * *

UNITED STATES PATENT AND TRADEMARK OFFICE
CERTIFICATE OF CORRECTION

PATENT NO. : 11,174,310 B2  
APPLICATION NO. : 16/345570  
DATED : November 16, 2021  
INVENTOR(S) : Asakura et al.

Page 1 of 1

It is certified that error appears in the above-identified patent and that said Letters Patent is hereby corrected as shown below:

In the Specification

In Column 13, Line 26, delete "(SEQ IS NO: 76)" and insert --(SEQ ID NO: 76)-- therefor In the Claims In Column 73, Line 39, in Claim 2, delete "MTh BP-02019." and insert --NITE BP-02019.-- therefor In Column 74, Lines 42-43, in Claim 8, delete "MTh BP-02020." and insert --NITE BP-02020.-- therefor Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 76

<210> SEQ ID NO 1
<211> LENGTH: 16
<212> TYPE: PRT
<213> ORGANISM: Artificial Sequence
<220> FEATURE:
<223> OTHER INFORMATION: An artificially synthesized peptide sequence

<400> SEQUENCE: 1

Gly Lys Gly Asp Pro Lys Lys Pro Arg Gly Lys Met Ser Ser Tyr Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: An artificially synthesized peptide sequence

<400> SEQUENCE: 2

Cys Arg Glu Glu His Lys Lys Lys His Pro Asp Ala Ser Val Asn Phe
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: An artificially synthesized peptide sequence

<400> SEQUENCE: 3

Lys Ala Asp Lys Ala Arg Tyr Glu Arg Glu Met Lys Thr Tyr
1               5                   10

<210> SEQ ID NO 4
<211> LENGTH: 82
<212> TYPE: PRT
<213> ORGANISM: Artificial Sequence
<220> FEATURE:
<223> OTHER INFORMATION: An artificially synthesized peptide sequence

<400> SEQUENCE: 4

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys

<210> SEQ ID NO 5
<211> LENGTH: 18
<212> TYPE: PRT
<213> ORGANISM: Artificial Sequence
<220> FEATURE:
<223> OTHER INFORMATION: An artificially synthesized peptide sequence

<400> SEQUENCE: 5

Met Trp Asn Asn Thr Ala Ala Asp Asp Lys Gln Pro Tyr Glu Lys Lys

```
1               5                  10                 15

Ala Ala

<210> SEQ ID NO 6
<211> LENGTH: 14
<212> TYPE: PRT
<213> ORGANISM: Artificial Sequence
<220> FEATURE:
<223> OTHER INFORMATION: An artificially synthesized peptide sequence

<400> SEQUENCE: 6

Lys Pro Asp Ala Ala Lys Lys Gly Val Val Lys Ala Glu Lys
1               5                  10

<210> SEQ ID NO 7
<211> LENGTH: 648
<212> TYPE: DNA
<213> ORGANISM: Homo sapiens

<400> SEQUENCE: 7
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaagcggaa caaggcccgt tatgaaagag aaatgaaaac ctatatccct     240
cccaaggggg agacaaaaaa gaagttcaag gatcccaatg cacccaagag gcctccttcg     300
gccttcttcc tcttctgctc tgagtatcgc ccaaaaatca aggagaacat cctggcctg     360 tccattggtg atgttgcgaa gaaactggga gagatgtgga ataacactgc tgcagatgac     420 aagcagccctt atgaaaagaa ggctgcgaag ctgaaggaaa atacgaaaaa ggatattgct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga tgaagaagaa gatgatgatg atgattaa                  648

<210> SEQ ID NO 8
<211> LENGTH: 20
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: misc_feature
<222> LOCATION: (13)..(14)
<223> OTHER INFORMATION: Xaa can be any naturally occurring amino acid

<400> SEQUENCE: 8

Gly Lys Met Ser Ser Tyr Ala Phe Phe Val Gln Thr Xaa Xaa Glu Glu
1               5                  10                 15

His Lys Lys Lys
              20

<210> SEQ ID NO 9
<211> LENGTH: 215
<212> TYPE: PRT
<213> ORGANISM: Homo sapiens

<400> SEQUENCE: 9

Met Gly Lys Gly Asp Pro Lys Lys Pro Arg Gly Lys Met Ser Ser Tyr
1               5                  10                 15

Ala Phe Phe Val Gln Thr Cys Arg Glu Glu His Lys Lys Lys His Pro
```

```
            20                  25                  30
Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
     50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Asp Glu Asp Glu
        195                 200                 205

Glu Glu Asp Asp Asp Asp Asp
    210                 215

<210> SEQ ID NO 10
<211> LENGTH: 215
<212> TYPE: PRT
<213> ORGANISM: Mus musculus

<400> SEQUENCE: 10

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
     50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175
```

Lys Ala Glu Lys Ser Lys Lys Lys Glu Glu Asp Glu Glu
            180                 185                 190

Asp Glu Glu Asp Glu Glu Glu Glu Glu Glu Asp Glu Asp Glu
            195                 200                 205

Glu Glu Asp Asp Asp Asp Glu
    210                 215

<210> SEQ ID NO 11
<211> LENGTH: 215
<212> TYPE: PRT
<213> ORGANISM: Rattus norvegicus

<400> SEQUENCE: 11

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Asp Glu Glu
            180                 185                 190

Asp Glu Glu Asp Glu Glu Glu Glu Glu Glu Asp Glu Asp Glu
            195                 200                 205

Glu Glu Asp Asp Asp Asp Glu
    210                 215

<210> SEQ ID NO 12
<211> LENGTH: 215
<212> TYPE: PRT
<213> ORGANISM: Oryctolagus cuniculus

<400> SEQUENCE: 12

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Asp Glu Glu Asp Glu Asp Glu
        195                 200                 205

Glu Glu Asp Asp Asp Asp Glu
    210                 215

<210> SEQ ID NO 13
<211> LENGTH: 215
<212> TYPE: PRT
<213> ORGANISM: Canis lupus familiaris

<400> SEQUENCE: 13

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Asp Glu Glu Asp Glu Asp Glu
        195                 200                 205

Glu Glu Asp Asp Asp Asp Glu
    210                 215

<210> SEQ ID NO 14
<211> LENGTH: 215
<212> TYPE: PRT
<213> ORGANISM: Felis catus

<400> SEQUENCE: 14

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Asp Glu Glu Glu
        195                 200                 205

Glu Glu Asp Asp Asp Asp Glu
    210                 215

<210> SEQ ID NO 15
<211> LENGTH: 215
<212> TYPE: PRT
<213> ORGANISM: Bos taurus

<400> SEQUENCE: 15

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
                180                 185                 190

Asp Glu Glu Asp Glu Glu Glu Glu Asp Glu Glu Asp Glu Glu
                195                 200                 205

Glu Glu Asp Asp Asp Asp Glu
        210                 215

<210> SEQ ID NO 16
<211> LENGTH: 215
<212> TYPE: PRT
<213> ORGANISM: Equus caballus

<400> SEQUENCE: 16

Met Gly Lys Gly Asp Pro Lys Lys Pro Arg Gly Lys Met Ser Ser Tyr
1               5                   10                  15

Ala Phe Phe Val Gln Thr Cys Arg Glu His Lys Lys Lys His Pro
                20                  25                  30

Asp Ala Ser Val Asn Phe Ser Glu Phe Ser Lys Lys Cys Ser Glu Arg
                35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
                180                 185                 190

Asp Glu Glu Asp Glu Glu Glu Glu Asp Glu Glu Asp Glu Glu
                195                 200                 205

Glu Glu Asp Asp Asp Asp Glu
        210                 215

<210> SEQ ID NO 17
<211> LENGTH: 215
<212> TYPE: PRT
<213> ORGANISM: Sus scrofa

<400> SEQUENCE: 17

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
            50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys His Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Glu Glu
                180                 185                 190

Asp Glu Glu Asp Glu Glu Glu Glu Asp Glu Glu Asp Glu Glu
            195                 200                 205

Glu Glu Asp Asp Asp Asp Glu
        210                 215

<210> SEQ ID NO 18
<211> LENGTH: 215
<212> TYPE: PRT
<213> ORGANISM: Capra hircus

<400> SEQUENCE: 18

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
            50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
```

```
                145                 150                 155                 160
Ala Tyr Arg Ala Lys Gly Lys Pro Asp Ala Ala Lys Lys Gly Val Val
                    165                 170                 175

Lys Ala Glu Lys Ser Lys Lys Lys Glu Glu Glu Asp Glu Glu
                    180                 185                 190

Asp Glu Glu Asp Glu Glu Glu Glu Asp Glu Asp Glu Glu Glu
                    195                 200                 205

Glu Glu Asp Asp Asp Asp Glu
            210                 215

<210> SEQ ID NO 19
<211> LENGTH: 215
<212> TYPE: PRT
<213> ORGANISM: Macaca mulatta

<400> SEQUENCE: 19

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
    115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                    165                 170                 175

Lys Ala Glu Lys Ser Lys Lys Lys Glu Glu Glu Asp Glu Glu
                    180                 185                 190

Asp Glu Glu Asp Glu Glu Glu Glu Asp Glu Asp Glu Glu Glu
                    195                 200                 205

Glu Glu Asp Asp Asp Asp Glu
            210                 215

<210> SEQ ID NO 20
<211> LENGTH: 215
<212> TYPE: PRT
<213> ORGANISM: Macaca fascicularis

<400> SEQUENCE: 20

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
```

```
                35                  40                  45
Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Asp Glu Asp Glu Asp Glu Asp Glu
                195                 200                 205

Glu Glu Asp Asp Asp Asp Glu
            210                 215

<210> SEQ ID NO 21
<211> LENGTH: 215
<212> TYPE: PRT
<213> ORGANISM: Pan troglodytes

<400> SEQUENCE: 21

Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190
```

-continued

Asp Glu Glu Asp Glu Glu Glu Asp Glu Asp Glu Asp Glu
        195                 200                 205

Glu Glu Asp Asp Asp Asp Glu
        210                 215

<210> SEQ ID NO 22
<211> LENGTH: 215
<212> TYPE: PRT
<213> ORGANISM: Gallus gallus

<400> SEQUENCE: 22

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Glu Asp Glu Asp
            180                 185                 190

Glu Asp Glu Glu Asp Glu Glu Asp Glu Glu Glu Glu Glu Glu Glu Glu
        195                 200                 205

Glu Asp Asp Asp Asp Glu
    210                 215

<210> SEQ ID NO 23
<211> LENGTH: 205
<212> TYPE: PRT
<213> ORGANISM: Danio rerio

<400> SEQUENCE: 23

Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys Lys His Pro Glu
                20                  25                  30

Ala Thr Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Leu Asp Lys Ala Arg Tyr Glu Arg Glu Met Lys Asn Tyr Ile Pro Pro
65                  70                  75                  80

-continued

```
Lys Gly Glu Lys Lys Lys Arg Phe Lys Asp Pro Asn Ala Pro Lys Arg
            85                  90                  95

Pro Pro Ser Ala Phe Phe Ile Phe Cys Ser Glu Phe Arg Pro Lys Val
        100                 105                 110

Lys Glu Glu Thr Pro Gly Leu Ser Ile Gly Asp Val Ala Lys Arg Leu
            115                 120                 125

Gly Glu Met Trp Asn Lys Ile Ser Ser Glu Glu Lys Gln Pro Tyr Glu
        130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Ala Ala Lys Ala Pro Ser
                165                 170                 175

Lys Pro Asp Lys Ala Asn Asp Glu Asp Glu Asp Asp Glu Glu Glu
            180                 185                 190

Asp Glu Asp Asp Asp Asp Glu Glu Glu Asp Asp Glu
            195                 200                 205
```

<210> SEQ ID NO 24
<211> LENGTH: 30
<212> TYPE: DNA
<213> ORGANISM: Mus musculus

<400> SEQUENCE: 24
gggttttcac tgagcacttc tggtatgggt        30

<210> SEQ ID NO 25
<211> LENGTH: 10
<212> TYPE: PRT
<213> ORGANISM: Mus musculus

<400> SEQUENCE: 25

```
Gly Phe Ser Leu Ser Thr Ser Gly Met Gly
1               5                   10
```

<210> SEQ ID NO 26
<211> LENGTH: 21
<212> TYPE: DNA
<213> ORGANISM: Mus musculus

<400> SEQUENCE: 26
atttggtggg atgatgataa g        21

<210> SEQ ID NO 27
<211> LENGTH: 7
<212> TYPE: PRT
<213> ORGANISM: Mus musculus

<400> SEQUENCE: 27

```
Ile Trp Trp Asp Asp Asp Lys
1               5
```

<210> SEQ ID NO 28
<211> LENGTH: 30
<212> TYPE: DNA
<213> ORGANISM: Mus musculus

<400> SEQUENCE: 28
gctcgaatag cggtagggta cttctatgtc        30

<210> SEQ ID NO 29
<211> LENGTH: 10

-continued

<212> TYPE: PRT
<213> ORGANISM: Mus musculus

<400> SEQUENCE: 29

Ala Arg Ile Ala Val Gly Tyr Phe Tyr Val
1               5                   10

<210> SEQ ID NO 30
<211> LENGTH: 30
<212> TYPE: DNA
<213> ORGANISM: Mus musculus

<400> SEQUENCE: 30
aaaagtgtca gtacatctgg ctatagttat                              30

<210> SEQ ID NO 31
<211> LENGTH: 10
<212> TYPE: PRT
<213> ORGANISM: Mus musculus

<400> SEQUENCE: 31

Lys Ser Val Ser Thr Ser Gly Tyr Ser Tyr
1               5                   10

<210> SEQ ID NO 32
<211> LENGTH: 9
<212> TYPE: DNA
<213> ORGANISM: Mus musculus

<400> SEQUENCE: 32 cttgtatcc                                                      9

<210> SEQ ID NO 33
<211> LENGTH: 3
<212> TYPE: PRT
<213> ORGANISM: Mus musculus

<400> SEQUENCE: 33

Leu Val Ser
1

<210> SEQ ID NO 34
<211> LENGTH: 66
<212> TYPE: DNA
<213> ORGANISM: Mus musculus

<400> SEQUENCE: 34
ctggaggagt caggccctgg gatattgcag ccctcccaga ccctcagtct gacttgttct    60
ttctct                                                              66

<210> SEQ ID NO 35
<211> LENGTH: 22
<212> TYPE: PRT
<213> ORGANISM: Mus musculus

<400> SEQUENCE: 35

Leu Glu Glu Ser Gly Pro Gly Ile Leu Gln Pro Ser Gln Thr Leu Ser
1               5                   10                  15

Leu Thr Cys Ser Phe Ser
            20

<210> SEQ ID NO 36
<211> LENGTH: 51

<212> TYPE: DNA
<213> ORGANISM: Mus musculus

<400> SEQUENCE: 36
gtaggctgga ttcgtcagcc ttcagggaag ggtctggagt ggctggcaca c        51

<210> SEQ ID NO 37
<211> LENGTH: 17
<212> TYPE: PRT
<213> ORGANISM: Mus musculus

<400> SEQUENCE: 37

Val Gly Trp Ile Arg Gln Pro Ser Gly Lys Gly Leu Glu Trp Leu Ala
1               5                   10                  15

His

<210> SEQ ID NO 38
<211> LENGTH: 114
<212> TYPE: DNA
<213> ORGANISM: Mus musculus

<400> SEQUENCE: 38
tactataaca cagccctgaa gagcgggctc acaatctcca aggatacctc caaaaaccag    60
gtcttcctca agatcgccag tgtggacact gcagatactg ccacatacta ctgt         114

<210> SEQ ID NO 39
<211> LENGTH: 38
<212> TYPE: PRT
<213> ORGANISM: Mus musculus

<400> SEQUENCE: 39

Tyr Tyr Asn Thr Ala Leu Lys Ser Gly Leu Thr Ile Ser Lys Asp Thr
1               5                   10                  15

Ser Lys Asn Gln Val Phe Leu Lys Ile Ala Ser Val Asp Thr Ala Asp
                20                  25                  30

Thr Ala Thr Tyr Tyr Cys
            35

<210> SEQ ID NO 40
<211> LENGTH: 78
<212> TYPE: DNA
<213> ORGANISM: Mus musculus

<400> SEQUENCE: 40
gacattgtgc tgacacagtc tcctgcttcc ttagctgtat ctctggggca gagggccacc    60
atctcataca gggccagc                                                  78

<210> SEQ ID NO 41
<211> LENGTH: 26
<212> TYPE: PRT
<213> ORGANISM: Mus musculus

<400> SEQUENCE: 41

Asp Ile Val Leu Thr Gln Ser Pro Ala Ser Leu Ala Val Ser Leu Gly
1               5                   10                  15

Gln Arg Ala Thr Ile Ser Tyr Arg Ala Ser
                20                  25

<210> SEQ ID NO 42
<211> LENGTH: 51
<212> TYPE: DNA

<213> ORGANISM: Mus musculus

<400> SEQUENCE: 42

| atgcactgga accaacagaa accaggacag ccacccagac tcctcatcta t | 51 |

<210> SEQ ID NO 43
<211> LENGTH: 17
<212> TYPE: PRT
<213> ORGANISM: Mus musculus

<400> SEQUENCE: 43

Met His Trp Asn Gln Gln Lys Pro Gly Gln Pro Pro Arg Leu Leu Ile
1               5                   10                  15

Tyr

<210> SEQ ID NO 44
<211> LENGTH: 99
<212> TYPE: DNA
<213> ORGANISM: Mus musculus

<400> SEQUENCE: 44

| aacctagaat ctggggtccc tgccaggttc agtggcagtg ggtctgggac agacttcacc | 60 |
| ctcaacatcc atcctgtgga ggaggaggat gctgcacca | 99 |

<210> SEQ ID NO 45
<211> LENGTH: 33
<212> TYPE: PRT
<213> ORGANISM: Mus musculus

<400> SEQUENCE: 45

Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
                20                  25                  30

Pro

<210> SEQ ID NO 46
<211> LENGTH: 381
<212> TYPE: DNA
<213> ORGANISM: Mus musculus

<400> SEQUENCE: 46

| gaggtgcagc tggaggagtc aggccctggg atattgcagc cctcccagac cctcagtctg | 60 |
| acttgttctt tctctgggtt ttcactgagc acttctggta tgggtgtagg ctggattcgt | 120 |
| cagccttcag ggaagggtct ggagtggctg gcacacattt ggtgggatga tgataagtac | 180 |
| tataacacag ccctgaagag cgggctcaca atctccaagg atacctccaa aaaccaggtc | 240 |
| ttcctcaaga tcgccagtgt ggacactgca gatactgcca catactactg tgctcgaata | 300 |
| gcggtagggt acttctatgt ctggggcgca gggaccacgg tcaccgtctc ctcagccaaa | 360 |
| acgacacccc catctgtcta t | 381 |

<210> SEQ ID NO 47
<211> LENGTH: 127
<212> TYPE: PRT
<213> ORGANISM: Mus musculus

<400> SEQUENCE: 47

Glu Val Gln Leu Glu Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
        20                  25                  30
Gly Met Gly Val Gly Trp Ile Arg Gln Pro Ser Gly Lys Gly Leu Glu
            35                  40                  45
Trp Leu Ala His Ile Trp Trp Asp Asp Lys Tyr Tyr Asn Thr Ala
50                  55                  60
Leu Lys Ser Gly Leu Thr Ile Ser Lys Asp Thr Ser Lys Asn Gln Val
65                  70                  75                  80
Phe Leu Lys Ile Ala Ser Val Asp Thr Ala Asp Thr Ala Thr Tyr Tyr
                85                  90                  95
Cys Ala Arg Ile Ala Val Gly Tyr Phe Tyr Val Trp Gly Ala Gly Thr
            100                 105                 110
Thr Val Thr Val Ser Ser Ala Lys Thr Thr Pro Pro Ser Val Tyr
            115                 120                 125

<210> SEQ ID NO 48
<211> LENGTH: 459
<212> TYPE: DNA
<213> ORGANISM: Mus musculus

<400> SEQUENCE: 48
tggatacagt tggtgcagca tcagcccgtt ttatttccag cttggtcccc cctccgaacg    60
tgtaagctcc ctaatgtgct gacagtaata ggttgaagca tcctctcttc cagctctcag   120
agatggagac agacacactc ctgttatggg tactgctgct ctgggttcca ggttccactg   180
gtgacattgt gctgacacag tctcctgctt ccttagctgt atctctgggg cagagggcca   240
ccatctcata cagggccagc aaaagtgtca gtacatctgg ctatagttat atgcactgga   300
accaacagaa accaggacag ccacccagac tcctcatcta tcttgtatcc aacctagaat   360
ctggggtccc tgccaggttc agtggcagtg gtctgggac agacttcacc ctcaacatcc   420
atcctgtgga ggaggaggat gctgcaccaa ctgtatcca                          459

<210> SEQ ID NO 49
<211> LENGTH: 128
<212> TYPE: PRT
<213> ORGANISM: Mus musculus

<400> SEQUENCE: 49

Cys Ala Asp Ser Asn Arg Leu Lys His Pro Leu Phe Gln Leu Ser Glu
1               5                   10                  15
Met Glu Thr Asp Thr Leu Leu Leu Trp Val Leu Leu Leu Trp Val Pro
            20                  25                  30
Gly Ser Thr Gly Asp Ile Val Leu Thr Gln Ser Pro Ala Ser Leu Ala
            35                  40                  45
Val Ser Leu Gly Gln Arg Ala Thr Ile Ser Tyr Arg Ala Ser Lys Ser
50                  55                  60
Val Ser Thr Ser Gly Tyr Ser Tyr Met His Trp Asn Gln Gln Lys Pro
65                  70                  75                  80
Gly Gln Pro Pro Arg Leu Leu Ile Tyr Leu Val Ser Asn Leu Glu Ser
                85                  90                  95
Gly Val Pro Ala Arg Phe Ser Gly Ser Gly Ser Gly Thr Asp Phe Thr
            100                 105                 110
Leu Asn Ile His Pro Val Glu Glu Glu Asp Ala Ala Pro Thr Val Ser
            115                 120                 125

```
<210> SEQ ID NO 50
<211> LENGTH: 24
<212> TYPE: DNA
<213> ORGANISM: Mus musculus

<400> SEQUENCE: 50
ggattcactt tcagtagcta tgcc                                          24

<210> SEQ ID NO 51
<211> LENGTH: 8
<212> TYPE: PRT
<213> ORGANISM: Mus musculus

<400> SEQUENCE: 51

Gly Phe Thr Phe Ser Ser Tyr Ala
1               5

<210> SEQ ID NO 52
<211> LENGTH: 24
<212> TYPE: DNA
<213> ORGANISM: Mus musculus

<400> SEQUENCE: 52
attagtagtg gtggtagtta cacc                                          24

<210> SEQ ID NO 53
<211> LENGTH: 8
<212> TYPE: PRT
<213> ORGANISM: Mus musculus

<400> SEQUENCE: 53

Ile Ser Ser Gly Gly Ser Tyr Thr
1               5

<210> SEQ ID NO 54
<211> LENGTH: 36
<212> TYPE: DNA
<213> ORGANISM: Mus musculus

<400> SEQUENCE: 54
gcaagacgac gggattacga cagggttttt gactac                             36

<210> SEQ ID NO 55
<211> LENGTH: 12
<212> TYPE: PRT
<213> ORGANISM: Mus musculus

<400> SEQUENCE: 55

Ala Arg Arg Arg Asp Tyr Asp Arg Gly Phe Asp Tyr
1               5                   10

<210> SEQ ID NO 56
<211> LENGTH: 75
<212> TYPE: DNA
<213> ORGANISM: Mus musculus

<400> SEQUENCE: 56
gaggtcaagc tggaggagtc tgggggaggc ttagtgaagc ctggagggtc cctgaaactc   60
tcctgtgcag cctct                                                    75

<210> SEQ ID NO 57
<211> LENGTH: 25
<212> TYPE: PRT
<213> ORGANISM: Mus musculus
```

<400> SEQUENCE: 57

Glu Val Lys Leu Glu Glu Ser Gly Gly Gly Leu Val Lys Pro Gly Gly
1               5                   10                  15

Ser Leu Lys Leu Ser Cys Ala Ala Ser
            20                  25

<210> SEQ ID NO 58
<211> LENGTH: 51
<212> TYPE: DNA
<213> ORGANISM: Mus musculus

<400> SEQUENCE: 58
atgtcttggg ttcgccagac tccggagaag aggctggagt gggtcgcaac c         51

<210> SEQ ID NO 59
<211> LENGTH: 17
<212> TYPE: PRT
<213> ORGANISM: Mus musculus

<400> SEQUENCE: 59

Met Ser Trp Val Arg Gln Thr Pro Glu Lys Arg Leu Glu Trp Val Ala
1               5                   10                  15

Thr

<210> SEQ ID NO 60
<211> LENGTH: 114
<212> TYPE: DNA
<213> ORGANISM: Mus musculus

<400> SEQUENCE: 60
tactatctag acagtgtgaa ggggcgattc accatctcca gagacaatgc caagaacacc    60
ctgtatctgc aaatgagcag tctgcggtct gaggacacgg ccgtgtatta ctgt         114

<210> SEQ ID NO 61
<211> LENGTH: 38
<212> TYPE: PRT
<213> ORGANISM: Mus musculus

<400> SEQUENCE: 61

Tyr Tyr Leu Asp Ser Val Lys Gly Arg Phe Thr Ile Ser Arg Asp Asn
1               5                   10                  15

Ala Lys Asn Thr Leu Tyr Leu Gln Met Ser Ser Leu Arg Ser Glu Asp
            20                  25                  30

Thr Ala Val Tyr Tyr Cys
        35

<210> SEQ ID NO 62
<211> LENGTH: 385
<212> TYPE: DNA
<213> ORGANISM: Mus musculus

<400> SEQUENCE: 62
tgaggtcaag ctggaggagt ctggggggagg cttagtgaag cctggagggt ccctgaaact    60
ctcctgtgca gcctctggat tcactttcag tagctatgcc atgtcttggg ttcgccagac    120
tccggagaag aggctggagt gggtcgcaac cattagtagt ggtggtagtt acacctacta    180
tctagacagt gtgaagggc gattcaccat ctccagagac aatgccaaga acaccctgta    240
tctgcaaatg agcagtctgc ggtctgagga cacggccgtg tattactgtg caagacgacg    300

```
ggattacgac aggggttttg actactgggg ccaaggcacc actctcacag tctcctcagc      360
caaaacgaca cccccatctg tctat                                            385
```

<210> SEQ ID NO 63
<211> LENGTH: 128
<212> TYPE: PRT
<213> ORGANISM: Mus musculus

<400> SEQUENCE: 63

```
Glu Val Lys Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Val Tyr Tyr Cys
                85                  90                  95

Ala Arg Arg Arg Asp Tyr Asp Arg Gly Phe Asp Tyr Trp Gly Gln Gly
            100                 105                 110

Thr Thr Leu Thr Val Ser Ser Ala Lys Thr Thr Pro Pro Ser Val Tyr
        115                 120                 125
```

<210> SEQ ID NO 64
<211> LENGTH: 27
<212> TYPE: DNA
<213> ORGANISM: Artificial Sequence
<220> FEATURE:
<223> OTHER INFORMATION: An artificially synthesized primer sequence

<400> SEQUENCE: 64

```
atagacagat gggggtgtcg ttttggc                                           27
```

<210> SEQ ID NO 65
<211> LENGTH: 20
<212> TYPE: DNA
<213> ORGANISM: Artificial Sequence
<220> FEATURE:
<223> OTHER INFORMATION: An artificially synthesized primer sequence
<220> FEATURE:
<221> NAME/KEY: misc_feature
<222> LOCATION: (6)..(6)
<223> OTHER INFORMATION: n is a, c, g, or t

<400> SEQUENCE: 65

```
sargtnmagc tgsagsagtc                                                   20
```

<210> SEQ ID NO 66
<211> LENGTH: 21
<212> TYPE: DNA
<213> ORGANISM: Artificial Sequence
<220> FEATURE:
<223> OTHER INFORMATION: An artificially synthesized primer sequence

<400> SEQUENCE: 66

```
ggatacagtt ggtgcagcat c                                                 21
```

<210> SEQ ID NO 67
<211> LENGTH: 24

<212> TYPE: DNA
<213> ORGANISM: Artificial Sequence
<220> FEATURE:
<223> OTHER INFORMATION: An artificially synthesized primer sequence

<400> SEQUENCE: 67
gayattgtgm tsacmcarwc tmca                                          24

<210> SEQ ID NO 68
<211> LENGTH: 18
<212> TYPE: DNA
<213> ORGANISM: Artificial Sequence
<220> FEATURE:
<223> OTHER INFORMATION: An artificially synthesized primer sequence

<400> SEQUENCE: 68
tgtaaaacga cggccagt                                                 18

<210> SEQ ID NO 69
<211> LENGTH: 18
<212> TYPE: DNA
<213> ORGANISM: Artificial Sequence
<220> FEATURE:
<223> OTHER INFORMATION: An artificially synthesized primer sequence

<400> SEQUENCE: 69
gaaacagcta tgaccatg                                                 18

<210> SEQ ID NO 70
<211> LENGTH: 115
<212> TYPE: PRT
<213> ORGANISM: Mus musculus

<400> SEQUENCE: 70

Leu Glu Glu Ser Gly Pro Gly Ile Leu Gln Pro Ser Gln Thr Leu Ser
1               5                   10                  15

Leu Thr Cys Ser Phe Ser Gly Phe Ser Leu Ser Thr Ser Gly Met Gly
            20                  25                  30

Val Gly Trp Ile Arg Gln Pro Ser Gly Lys Gly Leu Glu Trp Leu Ala
        35                  40                  45

His Ile Trp Trp Asp Asp Lys Tyr Tyr Asn Thr Ala Leu Lys Ser
    50                  55                  60

Gly Leu Thr Ile Ser Lys Asp Thr Ser Lys Asn Gln Val Phe Leu Lys
65                  70                  75                  80

Ile Ala Ser Val Asp Thr Ala Asp Thr Ala Thr Tyr Tyr Cys Ala Arg
                85                  90                  95

Ile Ala Val Gly Tyr Phe Tyr Val Trp Gly Ala Gly Thr Thr Val Thr
            100                 105                 110

Val Ser Ser
        115

<210> SEQ ID NO 71
<211> LENGTH: 346
<212> TYPE: DNA
<213> ORGANISM: Mus musculus

<400> SEQUENCE: 71
ctggaggagt caggccctgg gatattgcag ccctcccaga ccctcagtct gacttgttct    60
ttctctgggt tttcactgag cacttctggt atgggtgtag gctggattcg tcagccttca   120
gggaagggtc tggagtggct ggcacacatt tggtgggatg atgataagta ctataacaca   180

```
gccctgaaga gcgggctcac aatctccaag gatacctcca aaaaccaggt cttcctcaag    240
atcgccagtg tggacactgc agatactgcc acatactact gtgctcgaat agcggtaggg    300
tacttctatg tctggggcgc agggaccacg gtcaccgtct cctcag                   346
```

<210> SEQ ID NO 72
<211> LENGTH: 89
<212> TYPE: PRT
<213> ORGANISM: Mus musculus

<400> SEQUENCE: 72

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Pro
                85
```

<210> SEQ ID NO 73
<211> LENGTH: 267
<212> TYPE: DNA
<213> ORGANISM: Mus musculus

<400> SEQUENCE: 73

```
gacattgtgc tgacacagtc tcctgcttcc ttagctgtat ctctggggca gagggccacc     60
atctcataca gggccagcaa agtgtcagt acatctggct atagttatat gcactggaac    120
caacagaaac caggacagcc acccagactc ctcatctatc ttgtatccaa cctagaatct    180
ggggtccctg ccaggttcag tggcagtggg tctgggacag acttcaccct caacatccat    240
cctgtggagg aggaggatgc tgcacca                                         267
```

<210> SEQ ID NO 74
<211> LENGTH: 119
<212> TYPE: PRT
<213> ORGANISM: Mus musculus

<400> SEQUENCE: 74

```
Glu Val Lys Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Val Tyr Tyr Cys
                85                  90                  95

Ala Arg Arg Arg Asp Tyr Asp Arg Gly Phe Asp Tyr Trp Gly Gln Gly
            100                 105                 110
```

```
Thr Thr Leu Thr Val Ser Ser
        115

<210> SEQ ID NO 75
<211> LENGTH: 358
<212> TYPE: DNA
<213> ORGANISM: Mus musculus

<400> SEQUENCE: 75
gaggtcaagc tggaggagtc tggggggaggc ttagtgaagc ctggagggtc cctgaaactc      60
tcctgtgcag cctctggatt cactttcagt agctatgcca tgtcttgggt tcgccagact     120
ccggagaaga ggctggagtg ggtcgcaacc attagtagtg gtggtagtta cacctactat     180
ctagacagtg tgaaggggcg attcaccatc tccagagaca atgccaagaa caccctgtat     240
ctgcaaatga gcagtctgcg gtctgaggac acggccgtgt attactgtgc aagacgacgg     300
gattacgaca ggggtttga ctactgggc caaggcacca ctctcacagt ctcctcag       358

<210> SEQ ID NO 76
<211> LENGTH: 5
<212> TYPE: PRT
<213> ORGANISM: Artificial Sequence
<220> FEATURE:
<223> OTHER INFORMATION: An artificially synthesized peptide sequence

<400> SEQUENCE: 76

Gly Lys Met Ser Ser
1               5
```